US011701417B2

(12) United States Patent
Damron et al.

(10) Patent No.: US 11,701,417 B2
(45) Date of Patent: Jul. 18, 2023

(54) VACCINE FORMULATION TO PROTECT AGAINST PERTUSSIS

(71) Applicant: WEST VIRGINIA UNIVERSITY, Morgantown, WV (US)

(72) Inventors: Fredrick Heath Damron, Morgantown, WV (US); Mariette Barbier, Morgantown, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 16/832,490

(22) Filed: Mar. 27, 2020

(65) Prior Publication Data

US 2020/0405839 A1 Dec. 31, 2020

Related U.S. Application Data

(60) Provisional application No. 62/824,730, filed on Mar. 27, 2019.

(51) Int. Cl.
*A61K 39/09* (2006.01)
*A61P 31/04* (2006.01)
*A61K 39/02* (2006.01)
*A61K 39/39* (2006.01)

(52) U.S. Cl.
CPC ............ *A61K 39/099* (2013.01); *A61K 39/39* (2013.01); *A61P 31/04* (2018.01)

(58) Field of Classification Search
None
See application file for complete search history.

(56) References Cited

U.S. PATENT DOCUMENTS

| | | | | |
|---|---|---|---|---|
| 7,824,688 | B2 * | 11/2010 | Cassone | A61P 29/00 424/193.1 |
| 8,753,668 | B2 * | 6/2014 | Sedmak | A23K 10/10 424/442 |
| 2005/0220854 | A1 | 10/2005 | Maa et al. | |
| 2010/0034850 | A1 * | 2/2010 | De Hemptinne | A61K 39/099 424/203.1 |
| 2016/0303216 | A1 * | 10/2016 | Kapre | A61K 39/099 |
| 2018/0071380 | A1 * | 3/2018 | Makidon | A61P 43/00 |

FOREIGN PATENT DOCUMENTS

| | | |
|---|---|---|
| EP | 1667712 | 7/2010 |

OTHER PUBLICATIONS

Aiyer Harini, et al., J Vaccines Vaccin 2013, 4:1 http://dx.doi.org/10.4172/2157-7560.1000167.*
Orr et al. NPJ Vaccines. 2019; 4: 1. Published online Jan. 3, 2019. doi: 10.1038/s41541-018-0094-0.*
Grumezescu et al. (Microbial Production of Food Ingredients and Additives. Handbook of Food Bioengineering 2017, p. 362).*
Upadhyay et al. EXCLI J 2017; 16:210-228.*
Yan et al. Expert Opin. Biol. Ther. (2005) 5(5). 691-702.*
Agrawal, et al., "Human Dendritic Cells Activated via Dectin-1 Are Efficient at Priming Th17, Cytotoxic CD8 T and B Cell Responses", PLoS ONE, vol. 5, Issue 10, pp. 1-8. (Oct. 2010).
Allen, "Sustained protective immunity against Bordetella pertussis nasal colonization by intranasal immunization with a vaccineadjuvant combination that induces IL-17-secreting TRM cells", Society for Mucosal Immunology, 11, pp. 1763-1776. (2018).
Althouse, et al., "Asymptomatic transmission and the resurgence of *Bordetella pertussis*", Althouse and Scarpino BMC Medicine, 12 pages. (Downloaded May 8, 2020; DOI 10.1186/s12916-015-0382-8).
Ausiello, "Vaccine- and Antigen-Dependent Type 1 and Type 2 Cytokine Induction after Primary Vaccination of Infants with Whole-Cell or *Acellular pertussis* Vaccines", Infection and Immunity, vol. 65, No. 6, pp. 2168-2174. (Jun. 1997).
Ballister, et al., "In vitro self-assembly of tailorable nanotubes from a simple protein building block", PNAS, vol. 105, No. 10, pp. 3733-3738. (Mar. 11, 2008).
Barnard, et al., "Thl/Th2 cell dichotomy in acquired immunity to *Bordetellapertussis*: variables in the in vivo priming and in vitro cytokine detection techniques affect the classification of T-cell subsets as Thl, Th2 or ThO", Immunology, 87, pp. 372-380. (1996).
Baumann, et al., "Development and Clinical Use of an Oral Heat-Inactivated Whole Cell Pertussis Vaccine", Proceedings of the Fourth International Symposium on Pertussis, Joint IABS/WHO Meeting, Geneva, Switzerland, Develop. Biol., vol. 61, pp. 511-516. (1984).
Boehm, et al., "Evaluation of Adenylate Cyclase Toxoid Antigen in Acellular Pertussis Vaccines by Using a *Bordetella pertussis* Challenge Model in Mice", Infection and Immunity, vol. 86, Issue 10, 19 pages. (Oct. 2018).
Boehm, et al., "Intranasal acellular pertussis vaccine provides mucosal immunity and protects mice from *Bordetella pertussis*", npj Vaccines, 4, 40, 12 pages. (Downloaded May 11, 2020: https://doi.org/10.1038/s41541-019-0136-2).
Braun, et al., "Development of a freeze-stable formulation for vaccines containing aluminum salt adjuvants", Vaccine, 27, pp. 72-79. (2009).
Brickman, "The Ornithine Decarboxylase Gene odc Is Required for Alcaligin Siderophore Biosynthesis in *Bordetella* spp.: Putrescine Is a Precursor of Alcaligin", Journal of Bacteriology, vol. 178, No. 1, pp. 54-60. (Jan. 1996).
Brummelman, et al., "Roads to the development of improved pertussis vaccines paved by immunology", FEMS Pathogens and Disease, 73, 12 pages. (Sep. 7, 2015).
Carbonetti, "Contribution of pertussis toxin to the pathogenesis of pertussis disease", FEMS Pathogens and Disease, 73, 8 pages. (2015).

(Continued)

*Primary Examiner* — Oluwatosin A Ogunbiyi
(74) *Attorney, Agent, or Firm* — Kramer & Amado, P.C.

(57) ABSTRACT

A vaccine composition for intranasal administration includes a *Bordetella pertussis* antigen, and an effective adjuvant amount of a high molecular weight glucose polymer. The high molecular weight glucose polymer may be a beta-glucan. The *Bordetella pertussis* antigen may be an extracellular toxin, an adhesion protein, an outer membrane protein, a receptor protein, a fragment thereof, or a mixture thereof.

21 Claims, 16 Drawing Sheets
(9 of 16 Drawing Sheet(s) Filed in Color)

Specification includes a Sequence Listing.

(56) References Cited

OTHER PUBLICATIONS

Carbonetti, et al., "Pertussis Toxin and Adenylate Cyclase Toxin Provide a One-Two Punch for Establishment of *Bordetella pertussis* Infection of the Respiratory Tract", Infection and Immunity, vol. 73, No. 5, pp. 2698-2703. (May 2005).
Carbonetti, "Pertussis toxin and adenylate cyclase toxin: key virulence factors of *Bordetella pertussis* and cell biology tools", Future Microbiol. 5, pp. 455-469. (Mar. 2010).
Carbonetti, et al., "Pertussis Toxin Plays an Early Role in Respiratory Tract Colonization by *Bordetella pertussis*", Infection and Immunity, vol. 71, No. 11, pp. 6358-6366. (Nov. 2003).
Davis, et al., "CpG DNA Is a Potent Enhancer of Specific Immunity in Mice Immunized with Recombinant Hepatitis B Surface Antigen", The Journal of Immunology, 160, pp. 870-876. (1998).
Edwards, et al., "Comparison of 13 Acellular Pertussis Vaccines Overview and Serologic Response", Pediatrics, 96, 548, 12 pages. (1995).
Eisenbarth, et al., "Crucial role for the Nalp3 inflammasome in the immunostimulatory properties of aluminium adjuvants", Nature, 453(7198), pp. 122-1126. (Jun. 19, 2008).
Faulkner, et al., "Chapter 10: Pertussis", Vaccine Preventable Diseases Surveillance Manual, 14 pages. (Oct. 2017) (https://www.cdc.gov/vaccines/pubs/surv-manual/chpt10-pertussis.html).
Garson, "Preclinical Development of AS04", In: Davies G. (eds) Vaccine Adjuvants. Methods in Molecular Biology Methods and Protocols), vol. 626. Humana Press, Totowa, NJ (Dec. 28, 2009).
Goodman, et al., "Enzyme-Linked Immunosorbent Assay for Detection of Pertussis Immunoglobulin A in Nasopharyngeal Secretions as an Indicator of Recent Infection", Journal of Clinical Microbiology, vol. 13, No. 2, pp. 286-292. (Feb. 1981).
Goodridge, et al., "β-glucan Recognition by the Innate Immune System", Immunol Rev., 230(1), pp. 38-50. (Jul. 2009) (doi:10.1111/j.1600-065X.2009.00793.x.).
Gringhuis, et al., "Dectin-1 directs T helper cell differentiation by controlling noncanonical NF-jB activation through Raf-1 and Syk", Nature Immunology, vol. 10, No. 2, pp. 203-213. (Feb. 2009).
Hayden, et al., "The Extracytoplasmic Stress Factor, sE, Is Required to Maintain Cell Envelope Integrity in *Escherichia coli*", PLoS ONE, vol. 3, Issue 2, pp. 1-13. (Feb. 2008).
Higashi, "Curdlan Induces DC-Mediated Th17 Polarization via Jaggedl Activation in Human Dendritic Cells", Allergology International, vol. 59, No. 2, pp. 161-166. (2010).
Higgs, et al., "Immunity to the respiratory pathogen *Bordetella pertussis*", Mucosal Immunology, vol. 5, No. 5, pp. 485-500. (Sep. 2012).
Hill, et al., "Vaccination Coverage Among Children Aged 19-35 Months—United States, 2017", Morbidity and Mortality Weekly Report, vol. 67, No. 40, pp. 1123-1128. (Oct. 12, 2018).
Hogenesch, "Mechanism of immunopotentiation and safety of aluminum adjuvants", Frontiers of Immunology, vol. 3, Article 406, pp. 1-13. (Jan. 2013).
Kapil, et al., "Maternal Vaccination With a Monocomponent Pertussis Toxoid Vaccine Is Sufficient to Protect Infants in a Baboon Model of Whooping Cough", The Journal of Infectious Diseases, 217, pp. 1231-1236. (Apr. 15, 2018).
Kapil, et al., "Pertussis vaccines and protective immunity", Current Opinion in Immunology, 59, pp. 72-78. (2019).
Klein, et al., "Comparative Effectiveness of Acellular Versus Whole-Cell Pertussis Vaccines in Teenagers", Pediatrics, vol. 131, No. 6, pp. 1717-1723. (May 3, 2015).
Klein, et al., "Waning Protection after Fifth Dose of Acellular Pertussis Vaccine in Children", The New England Journal of Medicine, pp. 1012-1019. (Sep. 13, 2012).
Klein, et al., "Waning Tdap Effectiveness in Adolescents", Pediatrics, vol. 137, No. 3, pp. 1-11. (Mar. 2016).
Kumar, et al., "Involvement of the NLRP3 Inflammasome in Innate and Humoral Adaptive Immune Responses to Fungal B-Glucan", The Journal of Immunology, 183, pp. 8061-8067. (2009).
Locht, et al., "Live Attenuated Pertussis Vaccine BPZE1 Protects Baboons Against *Bordetella pertussis* Disease and Infection", The Journal of Infectious Diseases, 216, pp. 117-124. (Jul. 1, 2017) (https://doi.org/10.1093/infdis/jix254).
Martin, et al., "Pertactin-Negative *Bordetella pertussis* Strains: Evidence for a Possible Selective Advantage", CID, 60, pp. 223-227. (Jan. 15, 2015).
Mattoo, et al., "Molecular Pathogenesis, Epidemiology, and Clinical Manifestations of Respiratory Infections Due to *Bordetella pertussis* and Other *Bordetella* Subspecies", Clinical Microbiology Reviews, vol. 18, No. 2, pp. 326-382. (Apr. 2005).
McGuirk, et al., "Compartmentalization of T cell responses following respiratory infection with *Bordetella pertussis* hyporesponsiveness of lung T cells is associated with modulated expression of the co-stimulatory molecule CD28", Eur. J. Immunol. 28, pp. 153-163, (1998).
Melvin, et al., "*Bordetella pertussis* pathogenesis: current and future challenges", Nat Rev Microbiol., 12(4), pp. 274-288. (Apr. 2014).
Mills, "Immunity to *Bordetella pertussis*", Microbes and Infection, 3, pp. 655-677. (2001).
Misiak, et al., "IL-17-Producing Innate and Pathogen-Specific Tissue Resident Memory y T Cells Expand in the Lungs of *Bordetella pertussis* —Infected Mice", The Journal of Immunology, 198, pp. 363-374. (2016).
Motulsky, et al., "Detecting outliers when fitting data with nonlinear regression—a new method based on robust regression and the false discovery rate", BMC Bioinformatics, 7:123, pp. 1-20. (Mar. 9, 2006).
Pittman, et al., "History of the Development of Pertussis Vaccine", Symposium on Pertussis Evaluation and Research on Acellular Pertussis Vaccines Shizuoka, Japan, Develp. biol. Standard., vol. 73, pp. 13-29. (1990).
Redhead, et al., "Effective Immunization against *Bordetella pertussis* Respiratory Infection in Mice Is Dependent on Induction of Cell-Mediated Immunity", Infection and Immunity, vol. 61, No. 8, pp. 3190-3198. (Aug. 1993).
Ross, et al., "Relative Contribution of Th1 and Th17 Cells in Adaptive Immunity to *Bordetella pertussis*: Towards the Rational Design of an Improved Acellular Pertussis Vaccine", PLOS Pathogens, vol. 9, Issue 4, pp. 1-14. (Apr. 2013).
Rubin, et al., "Ther pertussis hypothesis: *Bordetella pertussis* colonization in the pathogenesis of Alzheimer's disease", Immunobiology, 222, pp. 228-240. (2017).
Skerry, et al., "A Live, Attenuated *Bordetella pertussis* Vaccine Provides Long-Term Protection against Virulent Challenge in a Murine Model", Clinical and Vaccine Immunology, pp. 187-193. (Feb. 2011).
Solans, et al., "IL-17-dependent SlgA-mediated protection against nasal *Bordetella pertussis* infection by live attenuated BPZE1 vaccine", Society for Mucosal Immunology, 11, pp. 1753-1762. (2018).
Solans, et al., "The Role of Mucosal Immunity in Pertussis", Frontiers in Immunology, vol. 9, Article 3068, pp. 1-10. (Jan. 2019).
Thorstensson, et al., "A Phase 1 Clinical Study of a Live Attenuated *Bordetella pertussis* Vaccine—BPZE1; A Single Centre, Double-Blind, Placebo-Controlled, Dose-Escalating Study of BPZE1 Given Intranasally to Healthy Adult Male Volunteers", PLoS ONE, vol. 9, Issue 1, pp. 1-10. (Jan. 2014).
Tuomanen, et al., "Characterization of Antibody Inhibiting Adherence of *Bordetella pertussis* to Human Respiratory Epithelial Cells", Journal of Clinical Microbiology, vol. 20, No. 2, pp. 167-170. (Aug. 1984).
Wilk, et al., "CD4 TRM Cells Following Infection and Immunization: Implications for More Effective Vaccine Design", Frontiers in Immunology, vol. 9, Article 1860, 8 pages. (Aug. 2018).
Wilk, et al., "Immunization with whole cell but not acellular pertussis vaccines primes CD4 TRM cells that sustain protective immunity against nasal colonization with *Bordetella pertussis*", Emerging Microbes & Infections, vol. 8, pp. 169-185. (2019).
Wilk, et al., "Lung CD4 Tissue-Resident Memory T Cells Mediate Adaptive Immunity Induced by Previous Infection of Mice with *Bordetella pertussis*", The Journal of Immunology, 199, pp. 233-243 (May 22, 2017).

(56) References Cited

OTHER PUBLICATIONS

Williams, et al., "*Bordetella pertussis* Strain Lacking Pertactin and Pertussis Toxin", Emerging Infectious Diseases, vol. 22, No. 2, pp. 319-322. (Feb. 2016).
Wolfe, et al., "Comparative Role of Immunoglobulin A in Protective Immunity against the Bordetellae", Infection and Immunity, vol. 75, No. 9, pp. 4416-4422. (Sep. 2007).
World Health Organization, "Pertussis vaccines: WHO position paper—Aug. 2015", Weekly epidemiological record, vol. 90, No. 35, pp. 433-460. (2015).
Wu, et al., "Th17-stimulating Protein Vaccines Confer Protection against Pseudomonas aeruginosa Pneumonia", American Journal of Respiratory and Critical Care Medicine, vol. 186. pp. 422-427. (2012).
Zhang, et al., "Decreased Leukocyte Accumulation and Delayed *Bordetella pertussis* Clearance in IL-6-/- Mice", J. Immunol., 186(8), pp. 4895-4904. (Apr. 15, 2011).
Zurita, et al., "A Pertussis Outer Membrane Vesicle-Based Vaccine Induces Lung-Resident Memory CD4 T Cells and Protection Against *Bordetella pertussis*, Including Pertactin Deficient Strains", Frontiers in Cellular and Infection Microbiology, vol. 9, Article 125, 11 pages. (Apr. 2019).
Transmittal Notification and International Search Report dated Jul. 21, 2021 re PCT/US2021/024557; 7 pgs.
Written Opinion of the International Searching Authority re PCT/US2021/024557 dated Jul. 21, 2021; 7 pgs.
NCBI, GenBank receptor No. WP_068926910.1, "Multispecies: TonB-dependent alcalligin siderophore receptor FauA [Bordetella]" Apr. 2, 2019.

* cited by examiner

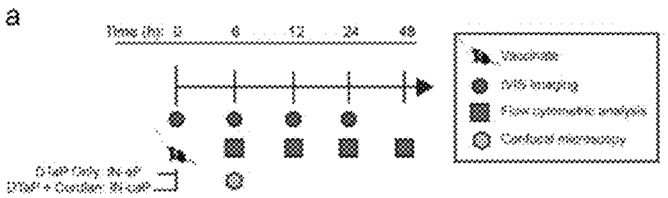
F IG. 6A

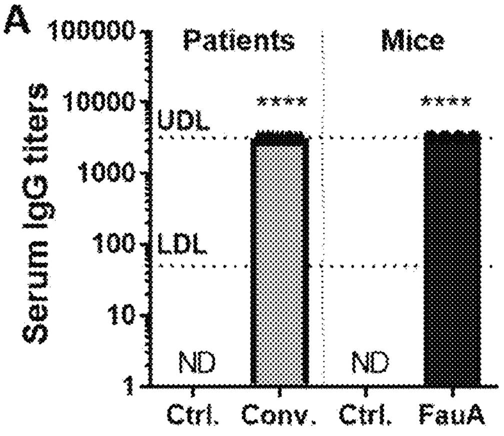
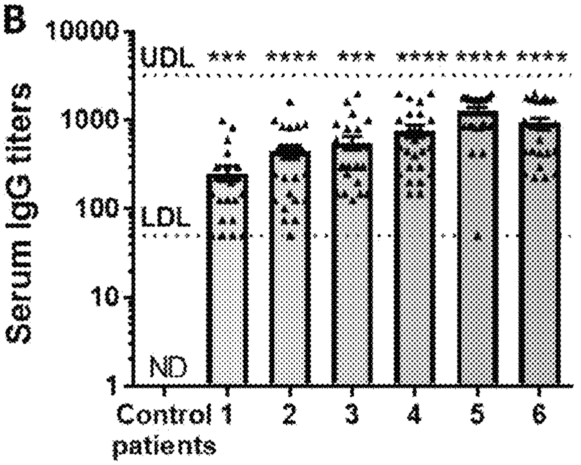
SEQ ID NO.
FIG. 13A
FIG. 13B
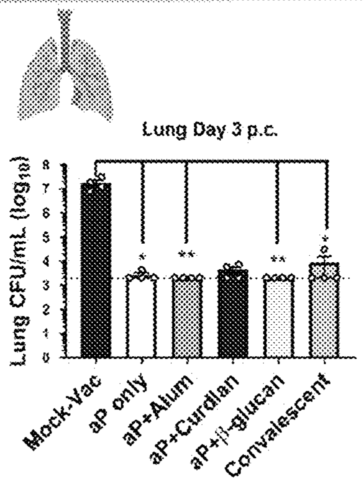
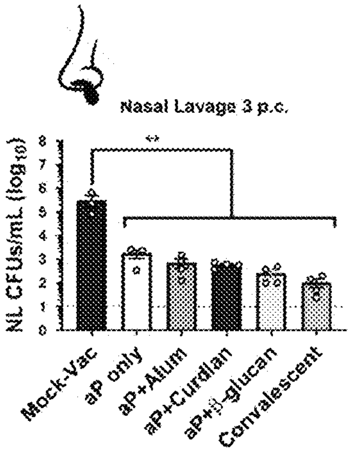
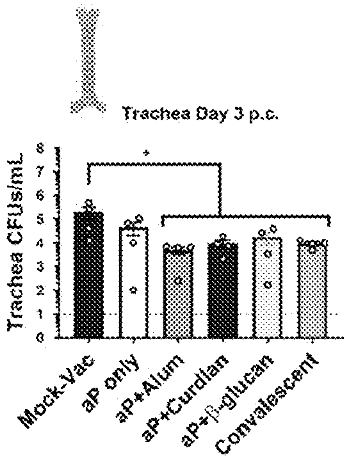
F IG. 14A
FIG. 14B
FIG. 14C

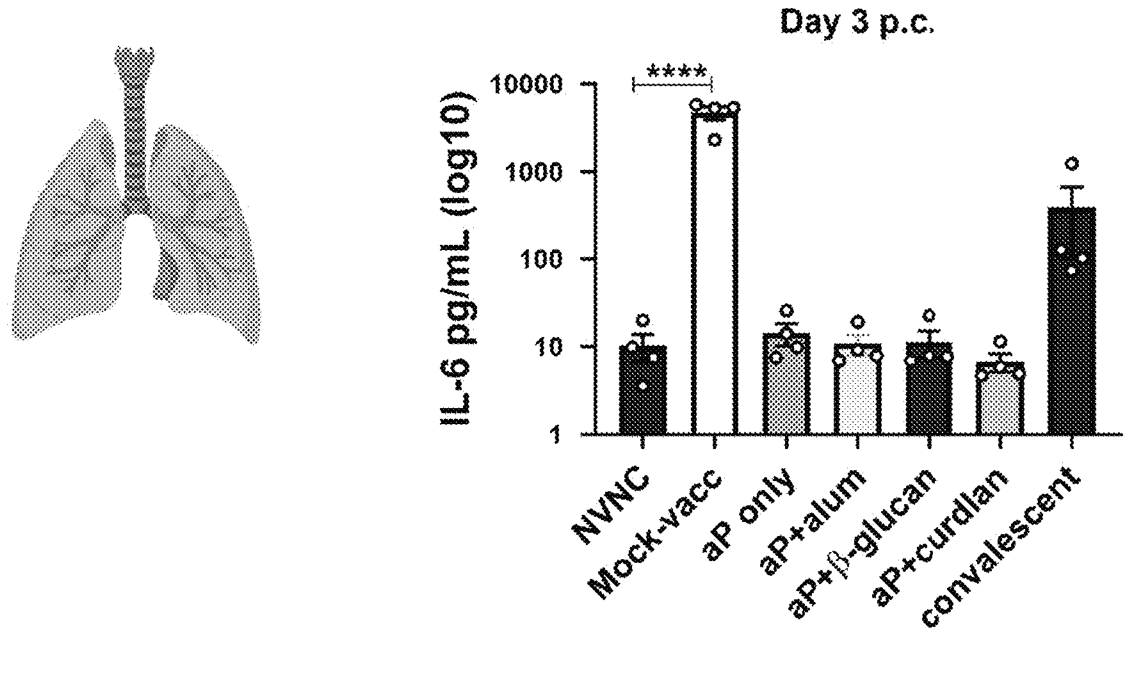
F IG. 15D

SEQUENCE LISTING

```
<160> NUMBER OF SEQ ID NOS: 22

<210> SEQ ID NO 1
<211> LENGTH: 36
<212> TYPE: PRT
<213> ORGANISM: Bordetella pertussis

<400> SEQUENCE: 1

Cys His Ser Asn Gly Phe Gly Ser Gly Phe Pro Leu Phe Tyr Ser Asp
1               5                   10                  15

Gly Ser Arg Thr Asp Phe Asn Arg Ser Val Ala Asn Asn Ala Pro Trp
            20                  25                  30

Ala Arg Gln Asp
        35


<210> SEQ ID NO 2
<211> LENGTH: 34
<212> TYPE: PRT
<213> ORGANISM: Bordetella pertussis

<400> SEQUENCE: 2

Cys Tyr Ala Met Val Gly Pro Ala Pro Ala Ile Gly Ser Phe Phe Asp
1               5                   10                  15
```

```
Trp Arg Arg Ala His Ile Gln Glu Pro Ser Trp Ala Asp Thr Leu Ser
            20                  25                  30

Pro Ala


<210> SEQ ID NO 3
<211> LENGTH: 19
<212> TYPE: PRT
<213> ORGANISM: Bordetella pertussis

<400> SEQUENCE: 3

Cys Phe Gln Pro Gln Asn Ala Arg Asp Thr Ser Gly Gly Ile Leu Pro
1               5                   10                  15

Pro Ile Lys


<210> SEQ ID NO 4
<211> LENGTH: 19
<212> TYPE: PRT
<213> ORGANISM: Bordetella pertussis

<400> SEQUENCE: 4

Cys Gln Val Ile Pro Gly Ser Ser Ile Pro Gly Phe Pro Asn Met Gln
1               5                   10                  15

Ala Ser Arg


<210> SEQ ID NO 5
<211> LENGTH: 22
<212> TYPE: PRT
<213> ORGANISM: Bordetella pertussis

<400> SEQUENCE: 5

Cys His Phe Thr Thr Lys Asp Ala Ser Gly Asn Pro Ile Asn Thr Asn
1               5                   10                  15

His Pro Arg Ser Leu Phe
            20


<210> SEQ ID NO 6
<211> LENGTH: 26
<212> TYPE: PRT
<213> ORGANISM: Bordetella pertussis

<400> SEQUENCE: 6

Cys Trp Gln Ser Arg Met Tyr Gln Ala Ala Ala Ser Pro Arg Gly Asn
1               5                   10                  15

Val Glu Val Glu Gln Asp Ser Tyr Ala Leu
            20                  25


<210> SEQ ID NO 7
<211> LENGTH: 33
<212> TYPE: PRT
<213> ORGANISM: Bordetella pertussis

<400> SEQUENCE: 7

Cys Tyr Asn Lys Thr Asn Pro Asp Ala Arg Asp Ile Asn Ala Gly His
1               5                   10                  15

Ala Asn Thr Ser Asp Asn Gly Asn Pro Ser Thr Ala Gly Arg Glu Gly
            20                  25                  30

Val


<210> SEQ ID NO 8
<211> LENGTH: 28
<212> TYPE: PRT
```

<213> ORGANISM: Bordetella pertussis

<400> SEQUENCE: 8

Cys Asn Leu Phe Ala Gly Asp Thr Met Asn Asn Ala Asn Ser Asp Phe
1 5 10 15

Ser Asp Ser Leu Tyr Gly Lys Glu Thr Asn Ala Met
20 25

<210> SEQ ID NO 9
<211> LENGTH: 26
<212> TYPE: PRT
<213> ORGANISM: Bordetella pertussis

<400> SEQUENCE: 9

Cys Ala Gly Thr Arg Gln Thr Tyr Thr Gly Gly Ala Ile Gly Gly Thr
1 5 10 15

Ala Pro Ala Asp Arg Asp Pro Lys Ser Arg
20 25

<210> SEQ ID NO 10
<211> LENGTH: 28
<212> TYPE: PRT
<213> ORGANISM: Bordetella pertussis

<400> SEQUENCE: 10

Cys Asn Ala Arg Gln Arg Glu Gly Leu Ala Gly Gly Pro Glu Gly Ala
1 5 10 15

Pro Thr Ala Gly Gly Tyr Asp Thr Ala Arg Leu Lys
20 25

<210> SEQ ID NO 11
<211> LENGTH: 31
<212> TYPE: PRT
<213> ORGANISM: Bordetella pertussis

<400> SEQUENCE: 11

Cys Asp Tyr Arg Asn Lys Ile Val Ala Gly Thr Asp Val Gln Tyr Arg
1 5 10 15

Leu Ala Asn Gly Ala Arg Val Leu Gln Trp Thr Asn Ser Gly Lys
20 25 30

<210> SEQ ID NO 12
<211> LENGTH: 48
<212> TYPE: PRT
<213> ORGANISM: Bordetella pertussis

<400> SEQUENCE: 12

Cys Tyr Lys Ala Pro Asn Leu Tyr Gln Ser Asn Pro Asn Tyr Leu Leu
1 5 10 15

Tyr Ser Arg Gly Asn Gly Cys Leu Ala Ser Gln Thr Asn Thr Asn Gly
20 25 30

Cys Tyr Leu Val Gly Asn Glu Asp Leu Ser Pro Glu Thr Ser Val Asn
35 40 45

<210> SEQ ID NO 13
<211> LENGTH: 29
<212> TYPE: PRT
<213> ORGANISM: Bordetella pertussis

<400> SEQUENCE: 13

Cys Thr Tyr Tyr Gly Lys Gln Glu Gly Pro Ser Thr Asn Val Arg Thr
1 5 10 15

-continued

```
Gly Val Glu Leu Asn Gly Asp Gly Arg Gln Thr Ile Ser
            20                  25
```

<210> SEQ ID NO 14
<211> LENGTH: 30
<212> TYPE: PRT
<213> ORGANISM: Bordetella pertussis

<400> SEQUENCE: 14

```
Cys Ser Asn Leu Phe Asp Lys Gln Leu Tyr Arg Glu Gly Asn Ala Ser
1               5                   10                  15

Ser Ala Gly Ala Ala Thr Tyr Asn Glu Pro Gly Arg Ala Tyr
            20                  25                  30
```

<210> SEQ ID NO 15
<211> LENGTH: 40
<212> TYPE: PRT
<213> ORGANISM: Bordetella pertussis

<400> SEQUENCE: 15

```
Cys Glu Tyr Phe Lys Arg Arg Ala Asp Leu Asp Gln Met Tyr Gln Gln
1               5                   10                  15

Gly Ala Gly Thr Ser Tyr Gln Tyr Gly Ala Asn Arg Thr His Glu Glu
            20                  25                  30

Thr Thr Arg Lys Arg Val Ser Leu
        35                  40
```

<210> SEQ ID NO 16
<211> LENGTH: 35
<212> TYPE: PRT
<213> ORGANISM: Bordetella pertussis

<400> SEQUENCE: 16

```
Cys Ala Gly Thr Arg Asn Gly His Asp Leu Asp Asn Arg Ala Asp Thr
1               5                   10                  15

Gly Gly Tyr Gly Ser Lys Arg Ser Gln Pro Ser Pro Glu Asp Tyr Ala
            20                  25                  30

Gln Asn Asn
        35
```

<210> SEQ ID NO 17
<211> LENGTH: 42
<212> TYPE: PRT
<213> ORGANISM: Bordetella pertussis

<400> SEQUENCE: 17

```
Cys Arg Leu Arg Leu Asp Ser Ser Gln Asp Ala Arg Arg Thr Arg Asp
1               5                   10                  15

Gly Arg Ala Tyr Ala Arg Pro Gly Asp Pro Tyr Phe Tyr Gly Tyr Pro
            20                  25                  30

Ser Gly Pro Tyr Gly Arg Ser Asn Ser Ile
        35                  40
```

<210> SEQ ID NO 18
<211> LENGTH: 49
<212> TYPE: PRT
<213> ORGANISM: Bordetella pertussis

<400> SEQUENCE: 18

```
Cys Glu Trp Tyr Gly Asn Arg Thr Glu Gln Tyr Ser Asp Gly Tyr Asp
1               5                   10                  15
```

```
Asn Cys Pro Ala Ile Pro Pro Gly Thr Pro Ala Pro Met Gly Pro Arg
            20                  25                  30

Leu Cys Asp Met Leu His Thr Asn Gln Ala Asp Met Pro Arg Val Lys
        35                  40                  45

Gly


<210> SEQ ID NO 19
<211> LENGTH: 36
<212> TYPE: PRT
<213> ORGANISM: Bordetella pertussis

<400> SEQUENCE: 19

Cys Leu Arg Tyr Asp His Tyr Glu Gln Lys Pro Gln Gln Gly Gly Gly
1               5                   10                  15

Tyr Gln Asn Asn Pro Asn Ala Gly Ala Leu Pro Pro Ser Ser Ser Gly
            20                  25                  30

Gly Arg Phe Ser
        35


<210> SEQ ID NO 20
<211> LENGTH: 50
<212> TYPE: PRT
<213> ORGANISM: Bordetella pertussis

<400> SEQUENCE: 20

Cys Gly Phe Gly Tyr Arg Ala Pro Ser Ala Thr Glu Leu Tyr Thr Asn
1               5                   10                  15

Tyr Gly Gly Pro Gly Thr Tyr Leu Arg Val Gly Asn Pro Ser Leu Lys
            20                  25                  30

Pro Glu Thr Ser Lys Gly Trp Glu Leu Gly Ala Arg Leu Gly Asp Asp
        35                  40                  45

Gln Leu
    50


<210> SEQ ID NO 21
<211> LENGTH: 33
<212> TYPE: PRT
<213> ORGANISM: Bordetella pertussis

<400> SEQUENCE: 21

Cys Ile Asp Lys Asn Val Pro Leu Gly Lys Gly Ser Pro Gln Trp Gln
1               5                   10                  15

Pro Ala Trp Asp Gly Gln Tyr Pro Leu Gly Val Thr Gly Leu Ala Asn
            20                  25                  30

Arg


<210> SEQ ID NO 22
<211> LENGTH: 27
<212> TYPE: PRT
<213> ORGANISM: Bordetella pertussis

<400> SEQUENCE: 22

Cys Thr Arg Arg Asp Asp Val Gln Tyr Pro Glu Ala Ser Ala Ser Ala
1               5                   10                  15

Arg Tyr Ala Asp Phe Gln Ala Pro Gly Tyr Gly
            20                  25
```

VACCINE FORMULATION TO PROTECT AGAINST PERTUSSIS

TECHNICAL FIELD

Various embodiments disclosed herein relate generally to a vaccine composition containing *Bordetella pertussis* (Bp) antigens and a high molecular weight polymer of glucose, more specifically for intranasal administration.

BACKGROUND

*Pertussis* is a bacterial, airborne disease that can be spread through coughing and sneezing. The Gram-negative bacteria invade the respiratory space, propagate, and releases bacterial toxins, causing pulmonary, and if untreated, cardiac dysfunction. Commonly known as whooping cough, *pertussis* can be deadly to young children or immune-compromised individuals. Currently, the standard vaccine for *pertussis*, is an acellular vaccine (aP; DTaP; Tdap), which presents several proteins from the *B. pertussis* pathogen to train the human immune system to respond with a humoral antibody response to clear the pathogen.

Despite high vaccine coverage, whooping cough has re-emerged as a major public health concern in the U.S. and the world. The incidence of *pertussis* has recently reached levels not seen since the 1950's. It is arguable that this increase is due to the switch from a whole cell vaccine (wP) to the currently used acellular vaccines. Originally formulated in the 1930-40's, the whole cell bacterial vaccine reduced the incidence of *pertussis* contraction but was associated with negative side effects. To remediate this, an acellular form of the vaccine was developed in the 1980's, which contained 2-5 proteins of *B. pertussis* bacteria adsorbed to alum adjuvant.

The acellular vaccines were developed to direct the immune response against the key components of the pathogen: 1) the extracellular *pertussis* toxin (PT), 2) the adhesion proteins (filamentous hemagglutinin (FHA) and fimbriae (FIM)), and 3) pertactin (PRN; an outer-membrane protein). aPs use aluminum hydroxide as the adjuvant to adsorb the antigens leading to a Th2 humoral response. In contrast, whole cell vaccines promote a Th1/Th17 response that activates both an IgG2a humoral response and cell mediated killing by macrophages and neutrophils. Natural immunity (due to infection) and wP immunization induced immunity lasted decades in humans.

Although acellular vaccines provide a safer alternative to whole cell vaccines, it appears that the acellular form has a shortened period of protection, resulting in a decreased efficacy in the years after immunization. This has led to a rise in the number of older children, and adolescents contracting whooping cough.

There are several hypotheses as to why whooping cough has re-emerged at such alarming rates. Data from the baboon model of *pertussis* has indicated that while aPs protect against the disease manifestation, the aPs do not prevent colonization or transmission of the pathogen. This increases the risk of contraction for neonates and those unable to be vaccinated. Human efficacy data also indicates that the protection wanes by as much as 35% each year after immunization. Furthermore, strains of *B. pertussis* are being clinically isolated do not express pertactin, which was originally characterized as one of the main virulence factors of *B. pertussis*. For these reasons, there is a need for a new generation of effective *pertussis* vaccines as returning to a whole cell vaccine is not an option due to the known risks.

SUMMARY OF EXEMPLARY EMBODIMENTS

Various embodiments recite a vaccine composition including a *B. pertussis* antigen and an effective adjuvant amount of a high molecular weight glucose polymer, wherein the composition is administered intranasally.

Various embodiments recite a vaccine composition including the *B. pertussis* antigens and an effective adjuvant amount of a β-glucan, wherein the β-glucan is selected from a group that includes curdlan, dextran, and baker's yeast beta-1,3/1,6-d-glucan.

Various embodiments recite a vaccine composition wherein the composition further includes an adenylate cyclase toxin antigen, such as RTX.

Various embodiments recite a vaccine composition wherein the composition induces a Th1/Th17 immune response.

Various embodiments further recite a method of immunizing a host against *pertussis* by administering intranasally to the host a vaccine composition including a *B. pertussis* antigen and an effective adjuvant amount of a high molecular weight glucose polymer.

Various embodiments further recite a method of enhancing the immune response of an intranasally administered *Bordetella pertussis* antigen that involves co-administering the antigen and a high molecular weight glucose polymer.

The present disclosure also describes a vaccine composition, comprising a *Bordetella pertussis* antigen, and an effective adjuvant amount of a high molecular weight glucose polymer, where the high molecular weight glucose polymer has a molecular weight of between 68 kDal and 680 kDal. The high molecular weight glucose polymer may be soluble or dispersible in water or aqueous base, and gellable in the presence of aqueous acid. The high molecular weight glucose polymer may be gellable in the respiratory system in the presence of acid and $CO_2$. The high molecular weight glucose polymer may be a beta-glucan, a 1,3-beta-glucan polymer, a 1,3-beta-glucan/1,4-beta-glucan copolymer, a 1,3-beta-glucan/1,6-beta-glucan copolymer, or a mixture thereof.

In various embodiments, the vaccine composition contains a *Bordetella pertussis* antigen which may be an extracellular toxin, an adhesion protein, an outer membrane protein, a receptor protein, fragments thereof, or mixtures thereof. The *Bordetella pertussis* antigen may be an extracellular *pertussis* toxin (PT), the adhesion proteins filamentous hemagglutinin (FHA) and fimbriae (FIM)), the outer membrane protein pertactin (PRN), the siderophore receptor protein FauA, the xenosiderophore receptor protein BfeA, the hemophore receptor protein BhuR, fragments thereof, or mixtures thereof. The *Bordetella pertussis* antigen may be the extracellular *pertussis* toxin (PT), the adhesion protein filamentous hemagglutinin (FHA), the siderophore receptor protein FauA, fragments thereof, or mixtures thereof.

In various embodiments, the composition is formulated for intranasal administration; for parenteral administration by subcutaneous (SC) injection, transdermal administration, intramuscular (IM) injection, or intradermal (ID) injection; or for non-parenteral administration by oral administration, intravaginal administration, pulmonary administration, ophthalmic administration, or rectal administration.

The current disclosure describes a vaccine composition for intranasal administration to a patient, including a *Bordetella pertussis* antigen, and an effective adjuvant amount of a high molecular weight glucose polymer, where the high molecular weight glucose polymer is configured to adhere to the airway of a patient, by forming a gel in the presence in the presence of $CO_2$ and aqueous acid.

The current disclosure describes a method of immunizing a host against *pertussis* by administering a vaccine composition including a *B. pertussis* antigen and an effective adjuvant amount of a high molecular weight glucose polymer intranasally to the host.

The current disclosure also describes a method of enhancing the immune response of an intranasally administered *B. pertussis* antigen that involves co-administering the antigen and a high molecular weight glucose polymer.

BRIEF DESCRIPTION OF THE DRAWINGS

In order to better understand various embodiments, reference is made to the accompanying drawings, wherein:

FIGS. 6A to 6F illustrate localization of acellular *pertussis* vaccine in the upper and lower respiratory system after IN vaccination. FIG. 6A shows a schematic of the vaccine tracking protocol. CD-1 mice were intranasally vaccinated with either fluorescent DTaP alone (IN-aP) or fluorescent DTaP with curdlan (IN-caP). Vaccine particle deposition in the lungs and nasal cavity was measured at 0, 6, 12, 24, and 48 h after immunization. FIG. 6B shows a representative image of Alexa Fluor labeled DTaP vaccine particles. FIG. 6C shows representative images of nasal cavity fluorescence at 6, 12, and 24 h after vaccination with IN-aP or IN-caP. The region of interest used for fluorescence quantification is shown in blue. FIG. 6D shows fluorescence measurements normalized to PBS control at 6, 12, and 24 h (n=4). Results shown as mean±SEM of total radiant efficiency, *P<0.05. P values were determined by multiple T-tests with Holm-Sidak post hoc test between IN-aP and IN-caP vaccinated mice. FIG. 6E shows representative plots at 12 h showing live, single cells that are $CD11b^+DTaP^+$. FIG. 6C shows flow cytometric analysis of $CD11b^+$ cells from the lung that contain or are bound to DTaP particles at 6, 12, 24, and 48 h post immunization. Results shown as mean±SEM, *P<0.05, *P<0.001, **P<0.0001 (n=4). P values were determined by one-way ANOVA with Dunnett's post hoc test comparing IN-aP immunized mice to control mock vaccinated mice.

FIG. 7A shows representative images of flash frozen lung sections 6 h after immunization with IN-aP and IN-cap. Fluorescent particles were detected using a 660 laser. Samples were counter-stained with NucBlue (blue) and ActinGreen (green). FIG. 7B shows quantifying fluorescent DTaP particles in lung tissue by determining the percentage area of particles per field of view (n=3-4, with averages of three images per lung). Results are shown as mean±SEM, *P<0.05. FIG. 7C shows representative images of paraffin embedded nasal cavity sections 6 h after immunization with IN-aP or IN-caP. FIG. 7D shows quantifying fluorescent DTaP particles in nasal tissue by determining the percentage area of particles per field of view. (n=3-4, with averages of three images per lung). P values were determined by one-way ANOVA with Tukey's post hoc test.

FIG. 8A and FIG. 8B show anti-PT and anti-FHA IgG production, respectively. Serum IgG1 and IgG2 antibody titers against *B. pertussis* (FIGS. 8C and 8D, respectively) were compared to mock vaccinated mice at day 3. Results are shown as mean±SEM, P<0.01, *P<0.001, ****P<0.0001 (n=3-8). P values were determined by one-way ANOVA with Dunnett's post hoc test compared to mock vaccinated mice.

FIG. 11A shows the percentage of live, CD11b+Gr-1hi neutrophils from a single cell suspension of the peripheral blood. FIG. 11B shows the percentages of CD11b+Gr-1hi neutrophils in single cell lung homogenates. FIG. 11C shows the percentage of CD4+ T cells that are CD62L-CD44+CD69+ isolated from the lung at day 3 pc. Results shown as means±SEM, *P<0.05 P<0.01, *P<0.001, ****P<0.0001 (n=4-8). P values were determined by one-way ANOVA with Dunnett's post hoc test compared to mock vaccinated mice.

FIGS. 13A and 13B show that *Pertussis* patients and mice immunized with FauA peptides have anti-FauA peptide antibodies. FIG. 13A shows ELISA detection of IgG anti-FauA in:

convalescent patient sera (n=23).

control patient sera (n=12).

mice vaccinated with FauA peptides (n=4); and control mouse sera (n=4).

FIG. 13B shows ELISA detection of IgG specific to various individual FauA peptides in convalescent or control patient sera. Each dot on the graph represents a different patient. Ctrl: control; ND: not detected; LDL: lower detection limit; UDL: upper detection limit.

FIGS. 14A to 14C show bacterial load in vaccinated mice three days after challenge by infection with *B. pertussis.*

Figure 15A:
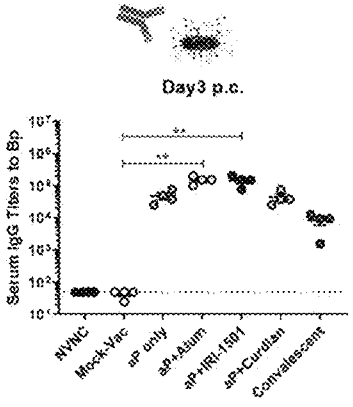
Figure 15B:
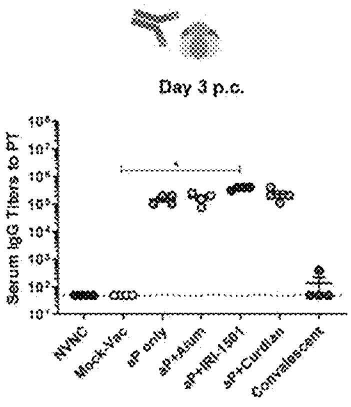
Figure 15C:
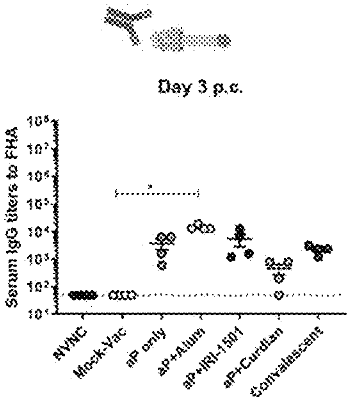

FIGS. 15A to 15C show serum antibody titers in vaccinated mice three days after challenge by infection with *B. pertussis*. FIG. 15D shows IL-6 levels in vaccinated mice three days after challenge by infection with *B. pertussis.*

Figure 16:
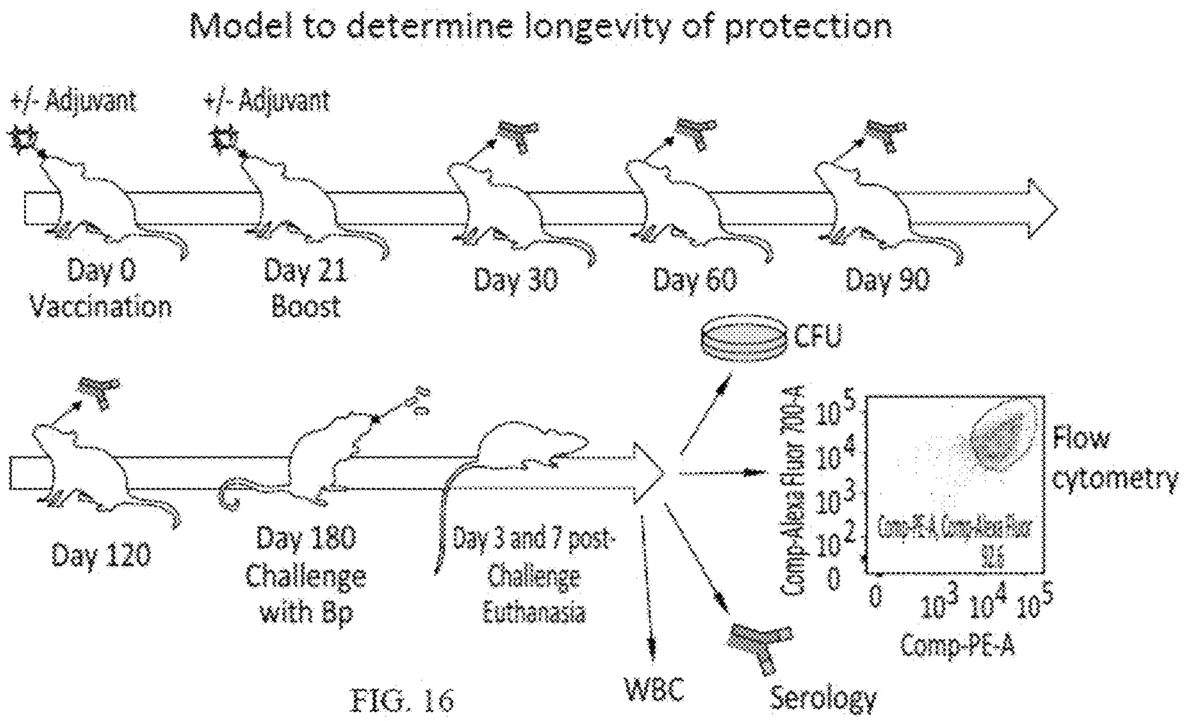

FIG. 16 shows a protocol for testing long-term protection against *pertussis* by intranasal vaccination.

Figure 17:
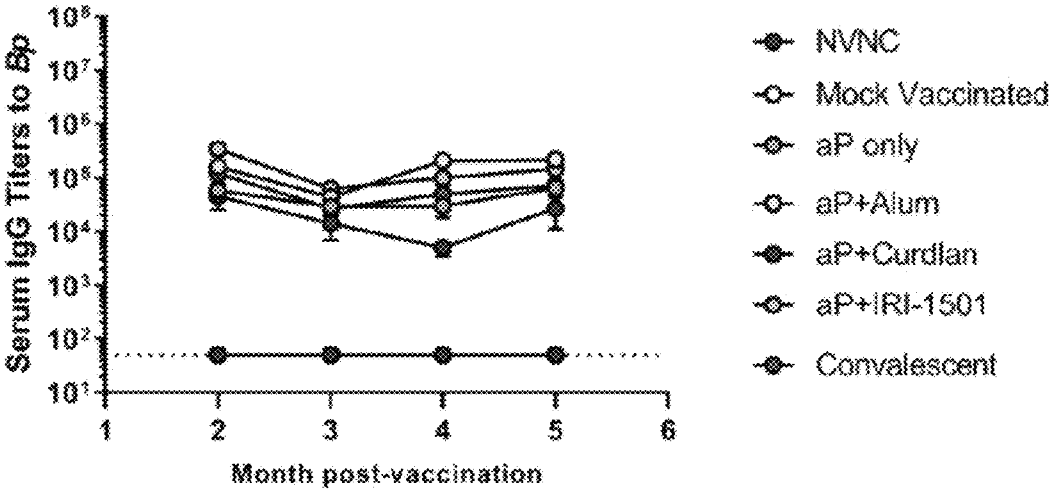

FIG. 17 shows serum antibody titers in vaccinated mice from 1 to 5 months following vaccination.

Figure 18:
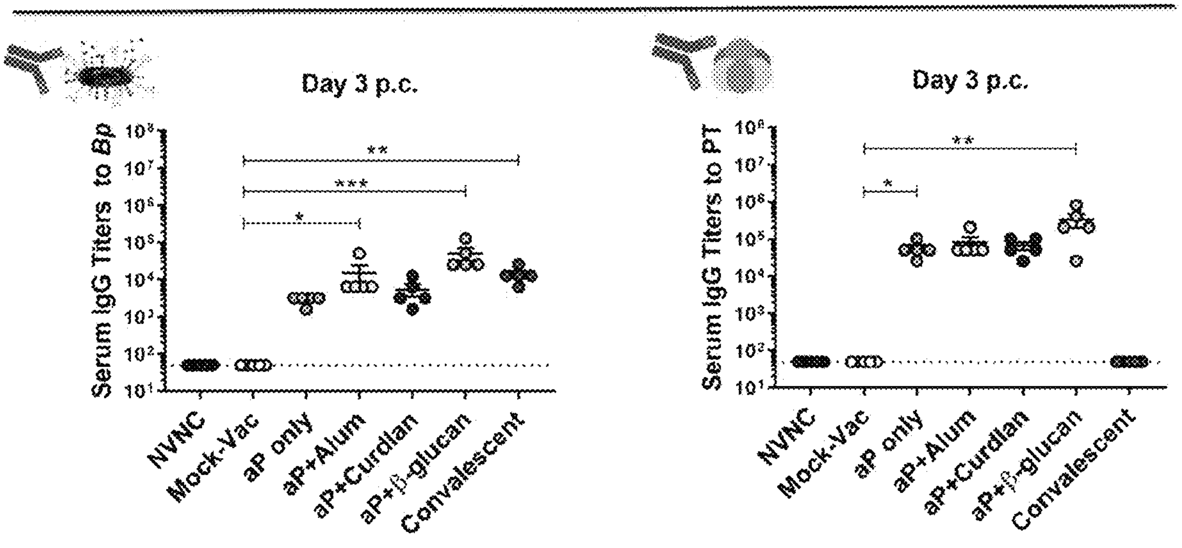

FIG. 18 shows serum antibody titers in vaccinated mice three days after challenge by infection with *B. pertussis* and 6 months after vaccination, where mice were vaccinated following the protocol of FIG. 16.

Figure 19A:
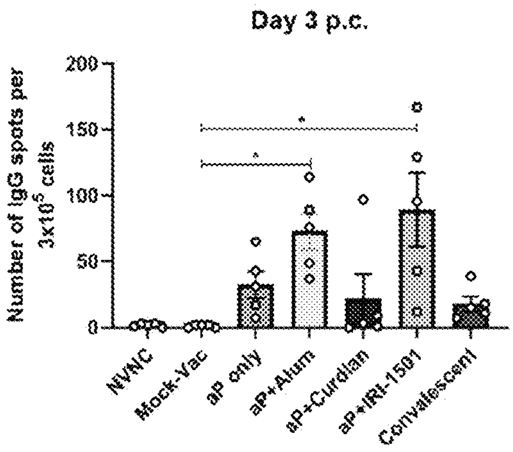
Figure 19B:
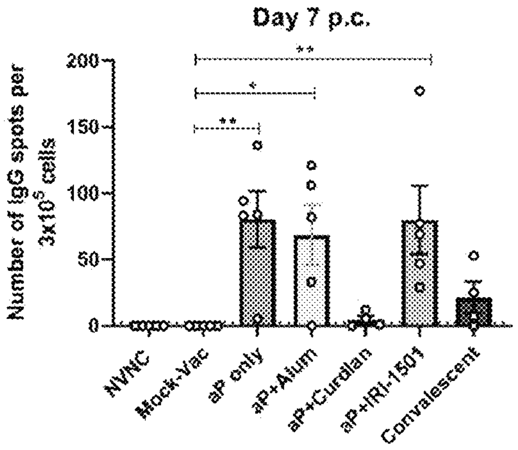

FIG. 19A and FIG. 19B show the impact of intranasal vaccination with aP, aP-alum, aP-curdlan, and aP-β-glucan (shown as aP+IRI-1501) on the number of *B. pertussis* antibody-secreting cells in bone marrow.

To facilitate understanding, identical reference numerals have been used to designate elements having substantially the same or similar structure or substantially the same or similar function.

DETAILED DESCRIPTION OF THE INVENTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or" refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Vaccine-induced protection in acellular *pertussis* vaccine (aP) immunized individuals has been associated with a robust antigen-specific IgG response to the components of the aP vaccines. Likewise, whole cell *pertussis* vaccine (wP) immunization also results in antigen-specific IgG responses; with the addition of a shift to a more diverse T cell response, inducing cell-mediated immunity. In the murine model, immunization through intramuscular (IM) and intraperitoneal (IP) administration has been well characterized demonstrating a Th1/Th17 response from wP immunized mice, and a Th2 with weak Th17 mediated response in aP immunized mice following *B. pertussis* challenge. However, these immunizations fail to induce the mucosal immune responses elicited from natural infection. Protection correlates with tissue resident memory T ($T_{RM}$) cells in the lung and nasal cavity of convalescent mice, that produce interleukin-17 (IL-17) and interferon-gamma (IFN-γ), although $T_{RM}$ activity in *pertussis* is yet to be studied in humans. $T_{RM}$ cells have been shown to persist in the respiratory tissue and expand upon re-challenge of a convalescent mouse with *B. pertussis*, as well as decrease bacterial burden upon adoptive transfer to naïve mice. More recently the expansion of this population has been observed following immunization by wP, a live-attenuated wP vaccine, an outer membrane vesicle vaccine, and intranasal administration of an aP vaccine with TLR9 and stimulator of interferon genes (STING) agonists.

The induction of a mucosal immune response to *B. pertussis* is associated with the production of secretory IgA antibodies (sIgA) in the nasal cavity. In humans previously infected with *B. pertussis*, IgA antibodies have been isolated from nasal secretions. *B. pertussis*-specific IgA antibodies isolated from convalescent patients have been shown to inhibit adherence of *B. pertussis* to respiratory epithelial cells in vitro, suggesting a protective role of IgA antibodies in mucosal immunity.

Conventional aP or DTaP vaccine does not contain a strong pro-inflammatory adjuvant. This disclosure describes IN aP or DTaP immunization alone, or with an additional pro-inflammatory adjuvant. A suitable pro-inflammatory adjuvant is a high molecular weight glucose polymer, which may be a beta-glucan, e.g., curdlan. Vaccines containing the adjuvant curdlan, a 1,3-beta-glucan derived from *Alcaligenes faecalis*, were formulated. This polysaccharide has immunostimulatory properties and forms a "sticky" gel at a neutral pH, or at an acidic pH in the presence of $CO_2$. The adjuvant has a relatively large particle size with dimensions sufficient to produce an inflammatory response. In certain embodiments, the high molecular weight glucose polymer may be a medium molecular weight glucan polymer with a molecular weight above 68 kDal, or between 68 kDal and 2MDal, or between 68 kDal and 680 kDal; this high molecular weight provides sufficient size for the inflammatory response from the soluble polymer. In various embodiments, the high molecular weight glucose polymer may be a whole glucan particle purified from a yeast. Such whole glucan particles typically have a particle size of 3 to 10 μm, 3.5 to 8 μm, or 4 to 6 μm, and may include residual proteins and/or lipids from yeast cells. The whole glucan particles may include 70% to 85%, 72% to 83%, or 75% to 80% 1,3-linked glucose units; 3% to 15%, or 5% to 10%, 1,6-linked glucose units; and 3% to 15%, or 5% to 10%, 1,3/1,6-linked glucose units. Whole glucan particles have sufficient size to trigger an inflammatory response from the polymer. In various embodiments, the glucose polymer may be conjugated to a protein, such as bovine serum albumin.

In another embodiment, the adjuvant includes particles having a minimum dimension of 3 jam, such as aluminum oxide particles. In another embodiment the majority of the adjuvant particles were between 3 to 10 μm, 3.5 to 8 μm, or 4 to 6 μm.

Curdlan and other β-glucan polymers has been shown to bind to dendritic cells through the ligand Dectin-1, thereby inducing expression of NF-xB leading to a Th1/Th17 mediated immune response as well as production of antigen-specific respiratory IgA antibodies and serum IgG antibodies. Dectin-1 is a receptor for β-glucans, which binds β-glucans and mediates the production of secretion of proinflammatory cytokines. Use of a β-glucan as an adjuvant may stimulate an immune response in a patient.

As discussed in the present disclosure, the gel properties of curdlan facilitate aP or DTaP localization in the upper respiratory tract. A significant reduction in bacteria burden is found following administration of intranasally administered aP or DTaP vaccines. High serum and respiratory antibody responses were measured, following intranasal administration of aP or DtaP, with and without curdlan. Mucosal vaccination with acellular vaccine containing a beta-glucan may be a strategy for decreasing incidence of *pertussis*.

It has now been found that immunization with *B. pertussis* antigens triggers a mucosal response similar to natural *B. pertussis* infection. Immunization may induce production of *pertussis* specific immunoglobulins that may: 1) mediate complement-dependent bacterial killing, 2) prevent colonization by blocking bacterial attachment, and 3) neutralize toxins at the site of infection. In some embodiments, a vaccine composition of the invention may provide a longer lasting and more effective form of the whooping cough vaccine, leading to decreased incidence of asymptomatic carriers and contraction by immune compromised and neonatal individuals.

In various embodiments of the invention, the vaccine composition may include *B. pertussis* antigens selected from a group that includes extracellular *pertussis* toxin (PT), the adhesion proteins filamentous hemagglutinin (FHA) and fimbriae (FIM), pertactin (PRN), and combinations thereof. The vaccine composition may include fragments of *B. pertussis* antigens selected from a group that includes PT, FHA, FIM, pertactin, and combinations thereof.

Additional proteins targeted for peptide vaccine development include the siderophore receptor FauA, the xenosiderophore receptor BfeA, and the hemophore receptor BhuR, and fragments thereof.

Antigen proteins, including those described above, were selected for use in the vaccine composition based on the following criteria:

- They are present on the surface of the organism, allowing for surface recognition and opsonophagocytosis.
- They have conserved sequences, with the sequence of the corresponding gene having:
  - at least 95% similarity across the clinical isolates tested, and
  - 85% similarity, 90% similarity, 95% similarity, or 98% similarity to corresponding genes in other *Bordetella* species.
- They are highly up-regulated during infection by *B. pertussis*.
- They are important for virulence, in that mutation of the antigen proteins negatively affects bacterial growth and pathogenesis.

Figure 1:
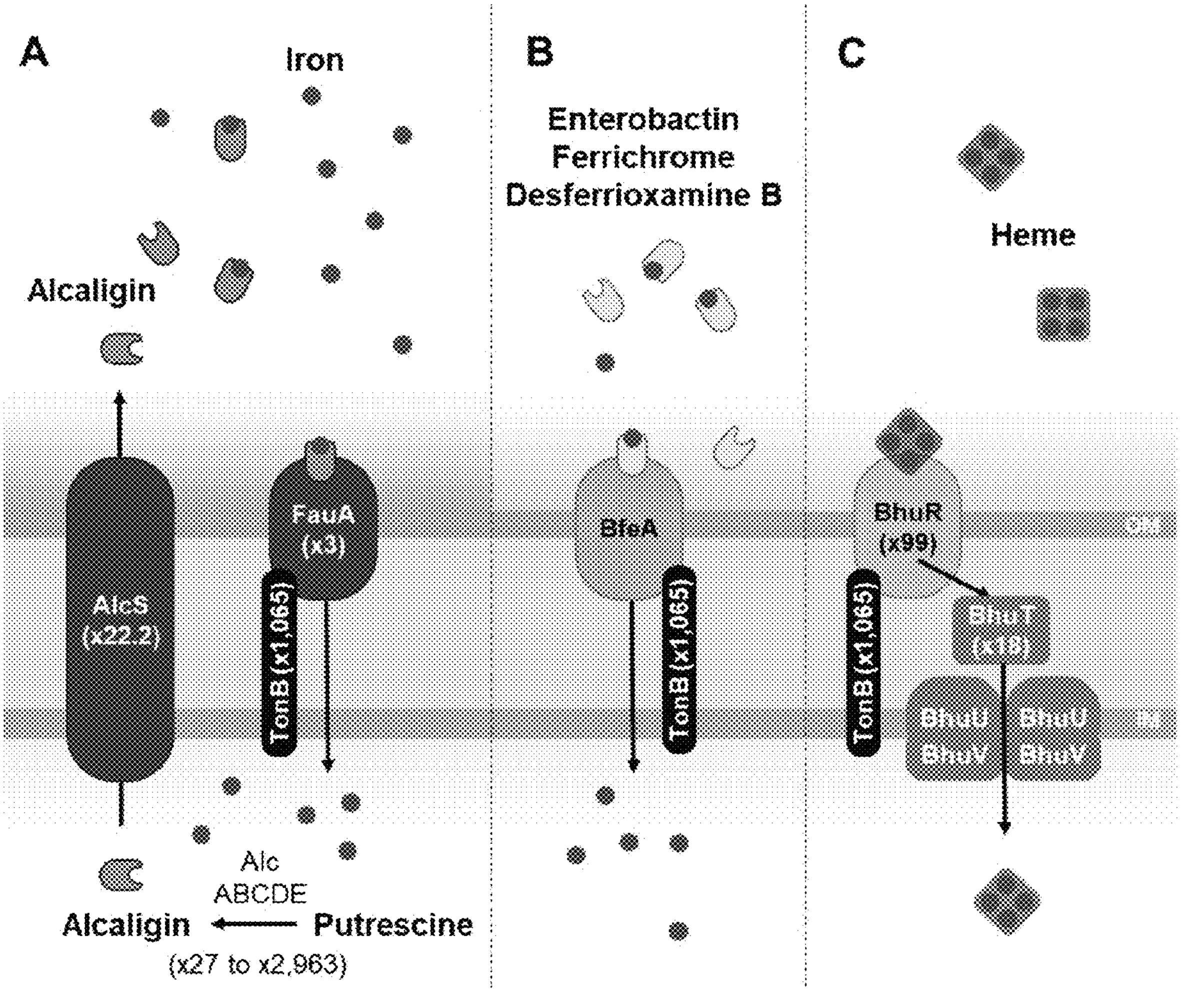
FIG. 1 shows iron and heme acquisition in *B. pertussis*. The model based on *B. pertussis* alcaligin, enterobactin and heme acquisition systems, and their homologues in other bacterial species. OM/IM: outer/inner membrane. In parentheses: fold changes in expression in vivo vs. in vitro.

For example, FIG. 1 shows iron and heme acquisition in *B. pertussis*. The model of FIG. 1 is based on *B. pertussis* alcaligin, enterobactin and heme acquisition systems. As seen in FIG. 1, FauA and BfeA are receptors for iron-carrying proteins, and BhuR is a receptor for a heme-carrying protein. These proteins are exposed on the outer membrane of *B. pertussis*, and are thus good candidates as antigens for a *B. pertussis* vaccine. Other proteins involved in iron or heme transport, like the transport protein TonB and the heme-transporting proteins BhuT, BhuU, and BhuV are less suitable antigen candidates, as they are not exposed on the outer membrane.

Acellular *pertussis* vaccines include PRN, PT, and FHA antigens (aP). As PRN and FHA antigens are harvested from the whole bacteria, these antigens may contain the lipooligosaccharide (LOS) endotoxin from the bacteria. The LOS endotoxin, if present, may serve as an antigen, and induce formation of antibodies against the *B. pertussis* bacteria, enhancing the formation of antibodies by the aP vaccine. In various embodiments, the LOS antigen may be added to the aP vaccine as a fourth antigen to enhance formation of *pertussis* antibodies.

The *pertussis* vaccine may be formulated with an adjuvant for administration. The adjuvant may be aluminum hydroxide (aP-alum), or a beta-glucan. In some cases, the beta-glucan may be a 1,3-beta-glucan (aP-beta-glucan) or curdlan (caP or aP-curdlan).

Figures 2A, 2B:
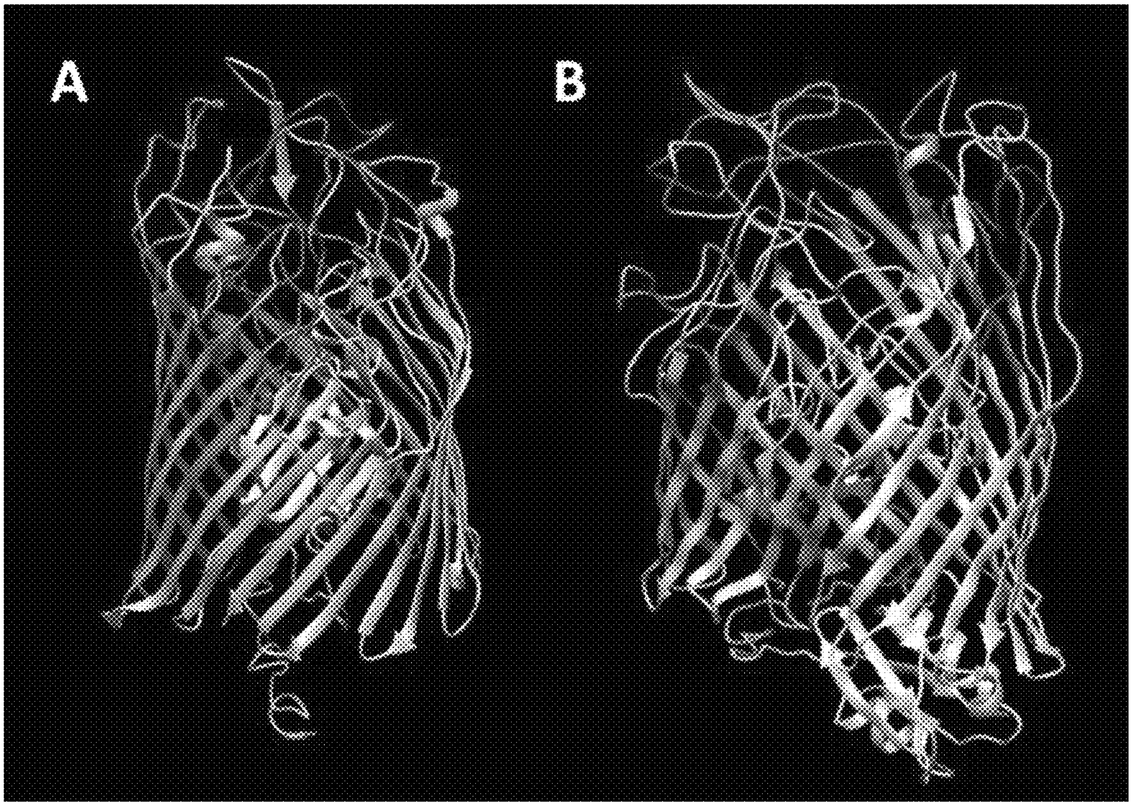
FIG. 2A and FIG. 2B show structures of the xenosiderophore receptor BfeA and the hemophore receptor BhuR, respectively. Sequences corresponding to antigenic peptides of Table 1 are highlighted in color.

As noted above fragments of *B. pertussis* proteins may be used as antigens. For example, extracellular regions of the proteins may be prepared and used as antigens. A bioinformatics pipeline may be used to identify the most immunogenic regions of proteins to be used as antigens for vaccination. A 3D protein structure analysis is performed. The structure analysis may use known crystal structures for a proposed antigen protein. Alternatively, the structure analysis may use a computational study to predict the protein structure. Structures of the xenosiderophore receptor BfeA and the hemophore receptor BhuR are shown in FIG. 2A and FIG. 2B, respectively.

The extracellular regions of the proposed antigen proteins are identified, and their immunogenicity is predicted based on their hydrophobicity and B cell epitope predictions. Using this approach, the sequences of various potential immunogenic regions were identified. Antigenic fragments based on these sequences were prepared. The antigen fragment peptides may then be modified by adding a cysteine residue on the N-terminus, and by conjugating them to a carrier protein. The carrier protein may be, but is not limited to, Keyhole Limpet Hemocyanin (KLH), diphtheria toxoid Cross-Reactive Material 197 (CRM197), or recombinant tetanus toxoid (rTTHc). Based on this approach, multiple potential antigenic peptide fragments based on FauA, BfeA, and BhuR were identified. These peptide fragments are presented in Table 1.

TABLE 1

| SEQ ID NO. | Peptide name | Peptide sequence |
|---|---|---|
| | Antigen Fragments based on FauA, BfeA, and BhuR. | |
| 1 | FauA peptide 1 (275-309) | CHSNGFGSGFPLFYSDGSRTDFNRSVANNAPW ARQD |
| 2 | FauA peptide 2 (409-441) | CYAMVGPAPAIGSFFDWRRAHIQEPSWADTLSP A |
| 3 | FauA peptide 3 (516-535) | CFQPQNARDTSGGILPPIK |
| 4 | FauA peptide 4 (567-584) | CQVIPGSSIPGFPNMQASR |
| 5 | FauA peptide 5 (617-633) | CHFTTKDASGNPINTNHPRSLF |
| 6 | FauA peptide 6 (658-680) | CWQSRMYQAAASPRGNVEVEQDSYAL |
| 7 | BfeA peptide 1 (226-257) | CYNKTNPDARDINAGHANTSDNGNPSTAGRE GV |
| 8 | BfeA peptide 2 (287-313) | CNLFAGDTMNNANSDFSDSLYGKFTNAM |
| 9 | BfeA peptide 3 (403-427) | CAGTRQTYTGGAIGGTAPADRDPKSR |
| 10 | BfeA peptide 4 (342-368) | CNARQREGLAGGPEGAPTAGGYDTARLK |
| 11 | BfeA peptide 5 (555-584) | CDYRNKIVAGTDVQYRLANGARVLQWTNSGK |
| 12 | BfeA peptide 6 (487-533) | CYKAPNLYQSNPNYLLYSRGNGCLASQTNTNG CYLVGNEDLSPETSVN |
| 13 | BfeA peptide 7 (650-677) | CTYYGKQEGPSTNVRTGVELNGDGRQTIS |
| 14 | BfeA peptide 8 (701-729) | CSNLFDKQLYREGNASSAGAATYNEPGRAY |
| 15 | BhuR peptide 1 (336-374) | CEYFKRRADLDQMYQQGAGTSYQYGANRTHE ETTRKRVSL |
| 16 | BhuR peptide 2 (283-316) | CAGTRNGHDLDNRADTGGYGSKRSQPSPEDY AQNN |
| 17 | BhuR peptide 3 (398-438) | CRLRLDSSQDARRTRDGRAYARPGDPYFYGYPS GPYGRSNSI |
| 18 | BhuR peptide 4 (466-513) | CEWYGNRTEQYSDGYDNCPAIPPGTPAPMGPR LCDMLHTNQADMPRVKG |
| 19 | BhuR peptide 5 (537-571) | CLRYDHYEQKPQQGGGYQNNPNAGALPPSSS GGRFS |
| 20 | BhuR peptide 6 (591-639) | CGFGYRAPSATELYTNYGGPGTYLRVGNPSLK PETSKGWELGARLGDDQL |
| 21 | BhuR peptide 7 (654-685) | CIDKNVPLGKGSPQWQPAWDGQYPLGVTGLA NR |
| 22 | BhuR peptide 8 (754-799) | CTRRDDVQYPEASASARYADFQAPGYG |

In one embodiment of the invention, the vaccine composition includes a *B. pertussis* antigen and an effective adjuvant amount of a high molecular weight polymer of glucose, such as β-glucan, dextran and the like. Preferred β-glucans include curdlan and baker's yeast beta-1,3/1,6-d-glucan. Curdlan is a bacterial and fungal β-1,3-glucan that binds to Dectin-1 receptors which are expressed on macrophages and dendritic cells.

The term "effective adjuvant amount" will be well understood by those skilled in the art, and includes an amount of a high molecular weight glucose polymer which is capable of stimulating the immune response to nasally administered antigens, i.e. an amount that increases the immune response of a nasally administered antigen composition.

In another embodiment, the vaccine composition of the invention may further be supplemented with an adenylate cyclase toxoid (ACT) which may improve efficacy of the vaccine composition by 1) generating anti-toxin antibodies against ACT, and 2) slowing vaccine-driven strain evolution. Suitable adenylate cyclase toxin antigens include purified repeats in the toxin domain (RTX antigen).

The vaccine composition of the invention may also contain additional adjuvants such as aluminum hydroxide.

The vaccine composition of the invention may be used as part of a prime-boost vaccine regimen. Conventional acellular *pertussis* vaccine (DTaP) is administered to human patients in five prime vaccinations at the following ages: 2 months, 4 months, 6 months, 15 to 18 months, 4 to 6 years. Periodic acellular *pertussis* vaccine boosts (TDaP) may be administered at age 11, and subsequently as needed. In a murine model, mice may be vaccinated with an aP vaccine as a prime, and then be given a boost vaccine 21 days later.

In one embodiment, the vaccine composition of the invention may be formulated for intranasal administration.

In other embodiments, the vaccine composition of the invention may be administered using alternative routes of administration including, without limitation, parenteral administration methods, such as subcutaneous (SC) injection, transdermal, intramuscular (IM), intradermal (ID), as well as non-parenteral, e.g., oral, intravaginal, pulmonary, ophthalmic and or rectal administration.

*Pertussis* toxin (PT) is an essential virulence factor, responsible for multiple factors in the pathogenesis of *B. pertussis*. PT facilitates infection by aiding in adherence to ciliated airway epithelial cells and through disruption of host innate immune cell recruitment to the site of infection. In numerous studies it has been demonstrated that neutralization of PT alone ablates symptoms of the disease. Neutralization of *pertussis* toxin at the site of infection may inhibit the systemic long-range activity of PT before colonization of the respiratory tract. Intranasal immunization with *pertussis* antigens may prime a protective systemic and mucosal immune response. Furthermore, the gel-like properties of curdlan may have a beneficial role in increasing antigen uptake.

EXAMPLES

The vaccines administered were prepared no longer than 1 h before administration. In Examples 1-3, INFANRIX (GSI) human vaccine (DTaP), and the National Institute for Biological Standards and Control WHO whole-cell *pertussis* vaccine (NIBSC code 94/532) were used as the aP acellular *pertussis* vaccine. The aP vaccine used in Examples 1-3 contains DTaP with formaldehyde killed *pertussis* toxoid. In Examples 4-8, genetically detoxified *pertussis* toxoid was used. The aP vaccine in Examples 4-8 contained PRN and PT antigens obtained from List Biologicals and FHA antigen obtained from ENZO bio. As the PRN and FHA antigens are harvested from *B. pertussis* bacteria, they may also contain the lipooligosaccharide (LOS) endotoxin from the bacteria.

Vaccines administered with curdlan were diluted with PBS to 1/12$^{th}$ of the human dose (based on total antigen content). Curdlan adjuvant was administered at 200 μg per mouse. A vaccine dose of 1/12$^{th}$ the human dose was the highest concentration of vaccine that was possible to use due to volume of vaccine required for the solubility of curdlan.

Curdlan (Invivogen, tlrl-curd) was prepared by dissolving 50 mg in 2.5 ml sterile purified water. Curdlan preparation was brought into solution by adding 100 μl 1N NaOH and vortexing. The curdlan suspension (20 mg/ml) was then sonicated for 10 mins and placed in 37° C. water bath until administration. At the time of vaccination, the vaccines containing curdlan were administered in a liquid form to reduce risk of choking due to excessive gel formation in the airway. IN administered mice recovered at the same rate as IP immunized mice. These experiments were conducted in accordance with the National Institutes of Health Guide for the care and use of laboratory animals. The protocols used were approved by West Virginia University Institutional Animal Care and Use Committees (WVU-ACUC protocol 1602000797). Curdlan, as used herein is a medium molecular weight glucan polymer, i.e., a polymer with a molecular weight of between 68 kDal and 680 kDal. The 1,3-β-glucan adjuvant, as used herein, is a whole glucan particle adjuvant having a particle size of 3 to 4 μm.

As comparison models, a group of mice were mock vaccinated with phosphate buffered saline (PBS). The mock vaccinated group was divided into a control group (Control or NVNC) which was not infected with *B. pertussis*, and a group which was infected with *B. pertussis* (Mock Vac). A third group of mice included unvaccinated mice recovering from *B. pertussis* infection (Convalescent)

Example 1

Figures 4A, 4B, 4C:
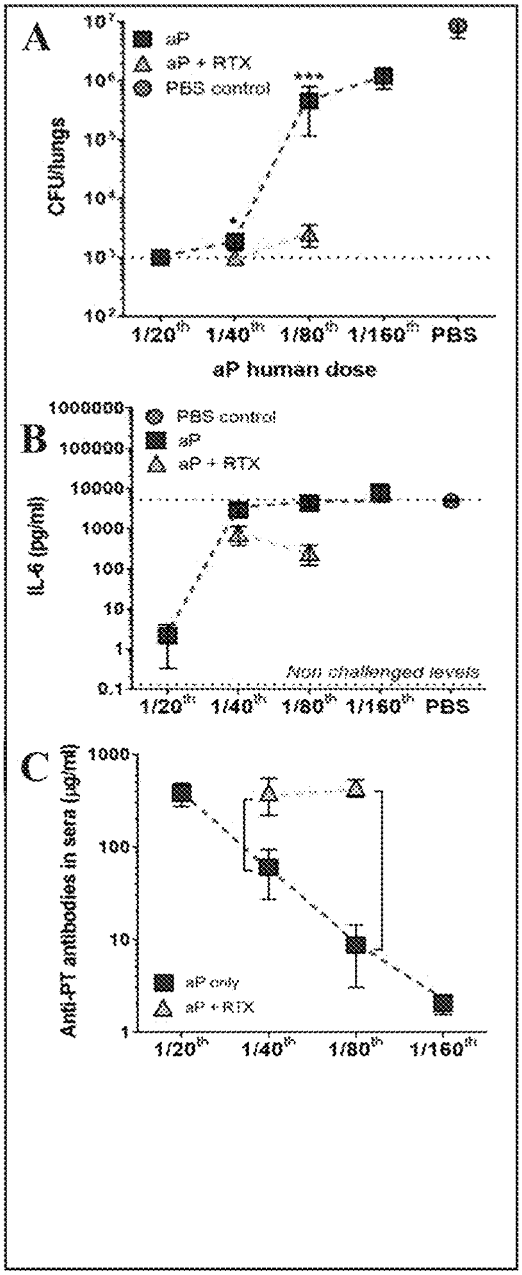
FIGS. 4A, 4B and 4C illustrate the synergistic improvement of DtaP administered by intraperitoneal injection (IP-DTaP) by inclusion of toxoid adenylate cyclase antigen (RTX) and show viable *B. pertussis* in lungs of mice at 3 days post challenge, enhanced production of anti-*pertussis* toxin due to inclusion of RTX, and decreased IL-6 due to inclusion of RTX, respectively.

Development of a Model to Evaluate ACT as an Antigen for Inclusion in aP aP vaccine lots are validated based on using high doses such as 1/5$^{th}$ human dose with intranasal *B. pertussis* challenge. However, those doses are not physiologically relevant to a mouse. Consequently, high doses of DTaP or Tdap antigens do not afford the ability to determine if addition of new antigens to the "base" vaccine can improve protection. In order to circumvent these issues, an approach was designed that could identify antigens that synergistically improve a vaccine. In these studies, 30 variables of data per mouse are collected to determine the correlates of protection. Lung IL-6 levels are an indication of 1) inflammation due to presence of pathogen and 2) ACT activity is known to activate IL-6 secretion. The vaccine minimum protective dose was identified as 1/40$^{th}$ based on the viable bacteria (FIG. 4A). 1/80$^{th}$ was selected as the dose to test inclusion of RTX antigen because of the amounts of viable bacteria in the respiratory tract (FIG. 4A), high IL-6 (FIG. 4B), and low total anti-PT (FIG. 4C).

Inclusion of RTX Antigen into the aP

Mice immunized with RTX alone with aluminum hydroxide are not protected against Bp challenge. However, when the 1/80$^{th}$ aP vaccine was supplemented with RTX antigen (5 μg), a significant decrease in bacterial burden was observed at day 3 (FIG. 4A) compared to 1/80$^{th}$ IP-aP alone. RTX inclusion also decreased IL-6 (FIG. 4B) which suggests that immunization neutralizes AC toxin activity in the murine host. High amounts of serum IgG were also detected that recognizes RTX using ELISA, confirming the immunization induced RTX-specific antibody production. Surprisingly, it was observed that inclusion of RTX enhanced anti-PT production as well (FIG. 4C) demonstrating potential adjuvant effects of RTX.

Example 2

Model of IN-caP Intranasal Immunization

For the studies, curdlan was selected as an adjuvant in order to induce a Th1/Th17 response which would mimic the wP or convalescent immunity. By interacting with the Dectin-1 receptor, curdlan primes naïve CD4+ T cells to differentiate to Th1 and Th17 T cells. In addition to its excellent adjuvant properties, curdlan can form a gel in the presence of carbon dioxide and at acidic pH. Thus, intranasal immunization with curdlan allows the antigen to adhere to the airway to allow uptake of the antigens by antigen presenting cells.

Figure 3:
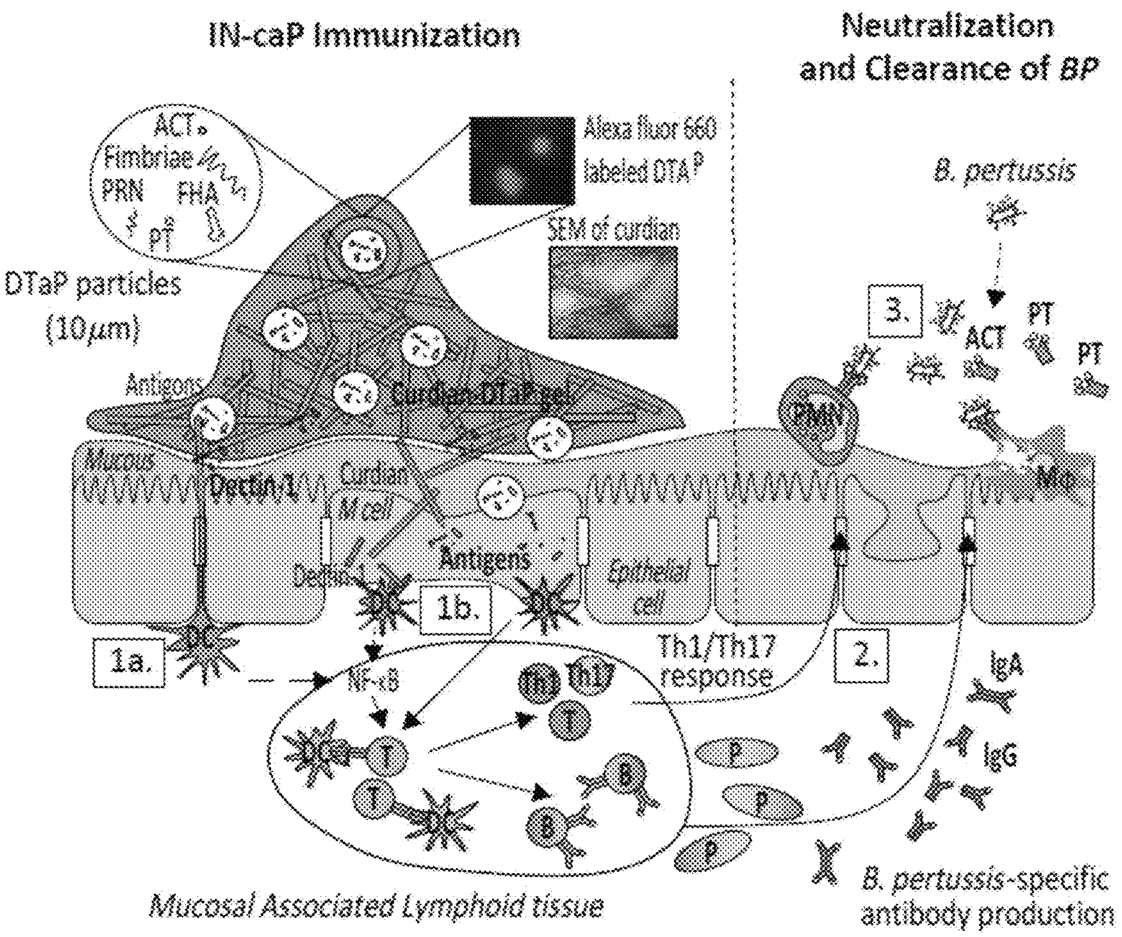
FIG. 3 illustrates a model of curdlan-DTaP immunization leading to T cell polarization and production of antibodies that recognize and neutralize infecting *B. pertussis.*

In the model presented in FIG. 3, curdlan encases the aP particles and facilitates their presentation to the mucosa as well as uptake of the antigens by antigen-presenting cells such as dendritic cells (DC).

In order to observe if curdlan facilitates the localization of the vaccine to the upper airway, DTaP was fluorescently labeled with Alexa fluor 660 dye (FIG. 3). It was observed that when curdlan was added as the adjuvant, three-fold more fluorescent signal was detected in the nasal flushes of mice compared to immunization without curdlan. The data suggests that curdlan gel facilitates adherence of the vaccine in the upper airway.

Figures 5A, 5B, 5C, 5D:
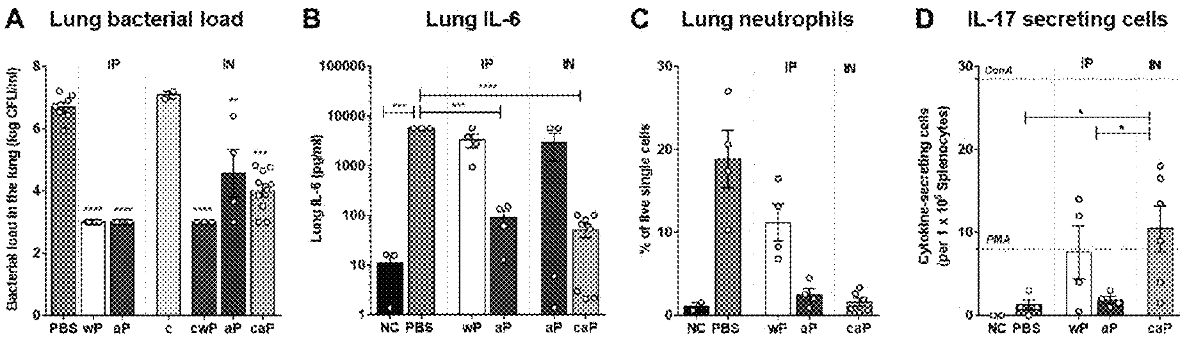
FIGS. 5A, 5B, 5C and 5D illustrate the bacterial burden, lung IL-6 production, lung neutrophil recruitment, and PT/FHA IL-17 production of splenocytes, respectively, in aP, wP, and IN-caP immunized mice.

IN-caP Intranasal Immunization Protects Against *B. pertussis* Challenge in Mice Mice were immunized with curdlan alone (200 μg/dose) with no antigens added. When mice were challenged with Bp, no protection was observed (FIG. 3A; curdlan only group). A $1/12^{th}$ human dose of DTaP (aP vaccine) was formulated and supplemented with curdlan (200 μg/dose). Intranasally administered curdlan-adjuvanted aP (IN-caP) immunized mice were then challenged with Bp. A decreased bacterial burden in the lung was observed 1 and 3 days post infection by over 3 logs (FIG. 5A). Limited protection was observed in the intranasally administered aP (IN-aP, aluminum hydroxide adjuvant), indicating that curdlan adjuvant facilitates induction of an adaptive response with IN immunization of aP. Compared to naïve mice, IN-caP immunized mice had reduced IL-6 (FIG. 5B) as well as low amounts of total neutrophils in the lung (FIG. 5C), which suggests that IN-caP immunization is protecting the mice from *B. pertussis* challenge.

IN-caP Immunization Results in FHA/PT Antigen-Specific IL-17 Producing Splenocytes The IN-caP vaccine contained curdlan and aluminum hydroxide adjuvants. To determine the T-cell response, Elispot analysis was performed on splenocytes of the immunized mice. Splenocytes were stimulated with PT and FHA antigens and it was observed that mice immunized with IN-caP induced significantly more IL-17-producing splenocytes than wP immunized mice (FIG. 5D). The data suggests that IN-caP induces a Th1/Th17 response.

TABLE 2

Analysis of antibody production in IN immunized mice.

| Vaccine | Bp challenged | FHA IgG | PT IgG | LOS IgG |
|---|---|---|---|---|
| none | NO | – | – | – |
| PBS | YES | – | – | – |
| IP-aP (1/5th human dose) | YES | +++ | +++ | – |
| IN-caP (1/12th human dose) | YES | +++ | +++ | – |
| IP-wP (1/5th human dose) YES | YES | +++ | – | +++ |
| IN-cwP (1/12th human dose) | YES | + | – | ++ |

To determine the antibody response triggered by IN-caP immunization, IgG production against FHA, PT, and lipooligosaccharide (LOS) antigens were measured in each vaccine group by ELISA. As seen in Table 2, both IP-aP and IN-caP induced production of FHA and PT IgGs, but did not induce production of LOS IgG. Intraperitoneally administered whole cell *pertussis* vaccine (IP-wP) and an intranasal whole cell *pertussis* vaccine containing curdlan (IN-cwP) induced production of FHA and LOS IgGs, but did not induce production of detectable anti-PT. Additionally, the immune response against FHA induced by IN-caP was stronger than the immune response against FHA induced by IN-cwP.

Example 3

Vaccination of Mice for Vaccine Particle Tracking

CD-1 (outbred; strain code 022) mice aged four weeks were obtained from Charles River Laboratories. At five weeks mice were anesthetized with 77 mg/kg ketamine and 7.7 mg/kg xylazine. Mice were administered 50 μl of vaccine or control, with 25 μl into each nostril (IN).

Tracking of DTaP in Respiratory System

DTaP vaccine particles were labeled using the Alexa Fluor 660 Protein Labeling Kit (Molecular Probes). Briefly, 0.5 ml of DTaP vaccine was added to 50 μl of 1 M sodium bicarbonate, then added to Alexa Fluor 660 dye stock. The mixture was incubated for 1 h at room temperature with agitation. The solution was concentrated by dialysis in phosphate-buffered saline overnight to remove unlabeled dye. Vaccine particles were examined using the Cy5 channel on an EVOS FL microscope. Particles were mounted on a slide and visualized using a 100× objective. Particle diameter was measured using ImageJ (version 1.52a) with the line segment tool in proportion to the scale bar. Four fields of view were measured to determine particle size and standard deviation. Labeled vaccine was used to immunize mice. At 0, 6, 12 and 24 h post vaccination, fluorescent signal was measured using an IVIS Spectrum (Xenogen), as shown in FIG. 6A. Mice were anesthetized using 3% isoflurane, mixed with oxygen prior to and throughout imaging. The following parameters were used: 1) A binning setting of 4 was kept constant for all images, 2) each image was quantified using the automatic image setting, 3) fluorescence photons were measured using total radiant efficiency of a common region of interest placed on the nasal cavity, and 4) measurements were normalized using Living Image (Xenogen ver. 2.5). Use of this quantification method accounted for variations in exposure between images.

At 6, 12, 24, and 48 h post vaccination, animals were euthanized to quantify DTaP in lungs by flow cytometry analysis, as shown in FIG. 6A. Lungs were removed, and homogenized using gentleMACS C tubes (Miltenyi Biotec) with enzymatic lung dissociation kit (Miltenyi Biotec, 130-095-927). All samples were blocked using Fc Block (BD), then labelled with Alexa Fluor 700— conjugated CD11b (Biolegend, 101222), DTaP particles were detected with Cy5 channel. Following a 1 h dark incubation labeled samples were washed, then fixed using 0.4% w/v paraformaldehyde overnight. Samples were resuspended in PBS and analyzed on an LSR Fortessa flow cytometer (BD). DTaP containing myeloid cells were classified as $CD11b^+DTaP^+$ single, live cells.

Detection of DTaP Particles in Lung and Nasal Cavity

Detection of DTaP particles in the lung and nasal cavity were confirmed using confocal imaging. Mock vaccinated and challenged mice were euthanized at 6 h post challenge, as shown in FIG. 6A. Prior to homogenization, the post-caval lobe of the mouse lung was removed. The post-caval lobe was flash frozen in OCT medium (Tissue Plus, Fisher Healthcare), using liquid nitrogen. The samples were stored at −80° C. until sectioning. Sectioned samples (6 μm) were fixed in acetone, then stained with ActinGreen Ready Probes (Invitrogen) and NucBlue Ready Probes (Invitrogen), using manufacturer protocols.

Skulls were removed from mouse, and the lower jawbone discarded. The skulls were fixed in formalin for 12 h at 4° C., then de-calcified at room temperature for 24 h, before samples were embedded in paraffin. Sectioned samples were de-paraffinized and rehydrated using xylene, and washes with decreasing ethanol concentrations (100 to 70%). An antigen retrieval step was performed using citrate buffer, where samples were heated to 98° C. for 20 mins. Samples were then stained as mentioned above. Samples were analyzed for DTaP particles in tissue and airway mucus using a Nikon confocal microscope. Images were acquired using DAPI, FITC, and Cy5 channels using a 100× oil immersion lens (100×/1.40 Nikon Plan Apo). DTaP particles were quantified using ImageJ. Briefly, the threshold tool was used to select only the fluorescent particles above background levels. Then, the threshold adjusted area was quantified using the analyze particles tool. Thus, the data is represented as the percentage of fluorescent particles per area of the total image field. Three image fields per sample were quantified and averaged per mouse.

*B. pertussis* Strains and Growth Conditions

*B. pertussis* strain UT25Sm1 was used for murine challenge in all experiments. UT25Sm1 was cultured on Bordet Gengou agar plus 15% defibrinated sheep's blood (Remel) with streptomycin 100 mg/ml. *B. pertussis* was incubated at 36° C. for 48h, then transferred to modified Stainer-Scholte liquid medium, without the cyclodextrin, heptakis. Liquid cultures were incubated for 24 h at 36° C., with shaking until reaching an $OD_{600}$ of ~0.6, at which time cultures were diluted for challenge dose.

Vaccination and *B. pertussis* Challenge

IN immunized mice received 50 μl of vaccine as described above. IP immunized mice received 2000 of vaccine injected into the peritoneal cavity. IN and IP immunized mice received the same antigen dose of $1/12^{th}$. Mice received a boost of the vaccines with the same concentrations twenty-one days after initial immunization. At thirty-five days post initial vaccination, mice were challenged with $2\times10^7$ CFU *B. pertussis* administered in 20 μl through nostrils. At days 1 and 3 post challenge (pc), mice were euthanized, blood and respiratory tissue were isolated as previously described.

Serological Analysis of *B. pertussis* Specific Antibodies

Serological responses specific to *B. pertussis* antigens were quantified by ELISA. High-binding microtiter plates were coated with PT (50 ng/well) (LIST Biologicals) and FHA (50 ng/well)(Enzo Life Sciences), as described in Boehm et al. Serological responses against UT25Sm1 were cultured to an $OD_{600}$ of 0.24 and microtiter plates coated with 50 μl of bacteria per well. Bound antibodies were detected using goat anti-mouse IgG, IgA, IgG2a, and IgG1 antibody conjugated to alkaline phosphatase (Southern Biotech). Positive antibody titers were determined using a baseline set at two times the average of blanks.

Quantification of Pulmonary and Blood APCs

To determine cell types infiltrating the lung and leukocytes present in peripheral blood, single cell suspensions from the tissues mentioned above were prepared. Briefly, lung tissue was homogenized by Dounce homogenizers, filtered with a 100 μm filter, and red blood cells were lysed for 2 min at 37° C. (Pharmlyse). Single cell populations were blocked by initial incubation with Fc Block (BD, 553141) for 15 min at 4° C. Cell populations were incubated in the dark with antibodies to cell surface markers for 1 h at 4° C. Neutrophil populations were identified using: PE-conjugated GR-1 (BD, 553128), Alexa Fluor 700-conjugated CD11b (Biolegend, 101222). Neutrophils were classified as $CD11b^+Gr\text{-}1^{hi}$ single, live cells. TRM populations were determined using: APC-Cy7-conjugated CD4 (Biolegend, 100526), BB515-conjugated CD44 (BD, 564587), APC-conjugated CD62L (BD, 553152), and BV421-conjugated CD69 (BD, 562920).

Lung Homogenate Cytokine Analysis

To quantify inflammatory cytokines at the site of infection, lung homogenate supernatant was prepared and stored at −80° C., as described in prior work. Quantitative analysis of cytokines was performed using Meso Scale Discovery cytokine kits: V-PLEX pro-inflammatory panel (K15048D) and IL-17A V-PLEX (K152RFD), per the manufacturer's instructions.

Statistical Analysis

Experiments in the study were performed with 3 to 8 biological replicates. Data were analyzed using GraphPad Prism 7. ROUT method was used to removed outliers. Comparisons between groups were performed using one-way analysis of variance (ANOVA) with Dunnett's and Tukey's post hoc tests. Comparisons between groups with or without curdlan were analyzed by two-tailed unpaired t-test, when applicable multiple T-tests with Holm-Sidak post hoc test were applied to curdlan inclusion groups.

Acellular *Pertussis* Vaccine was Retained in the Upper and Lower Respiratory Tract when Administered by Intranasal Administration.

Figure 6B:
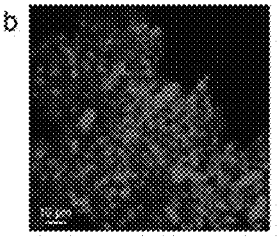
Figure 6C:
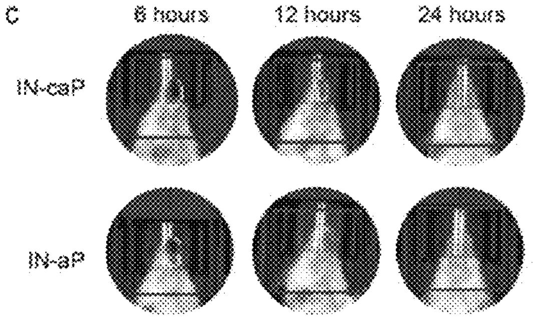
Figure 6D:
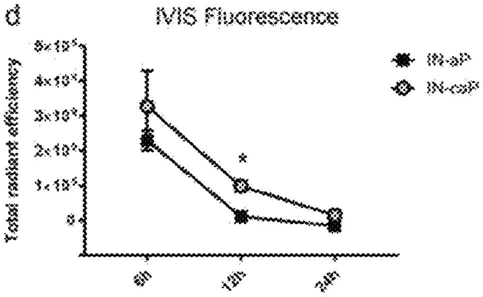

To determine if use of curdlan would increase vaccine retention in the respiratory system, CD-1 mice were intranasally (IN) vaccinated with commercially available DTaP (IN-aP), DTaP with curdlan (IN-caP), or phosphate-buffered saline (PBS; mock vaccinated) and the vaccine for up to 48 h after vaccination. The protocol is illustrated in FIG. 6A. To visualize vaccine presence in the respiratory system, DTaP vaccine particles were labeled with a fluorescent fluorophore (FIG. 6B). The size of the labeled particles was measured, and determined to be 1.52±0.76 μm, on average. Using in vivo animal imaging, we observed fluorescently labeled DTaP particles in the nasal cavity at 6, 12 and 24 h post-vaccination (FIG. 6C). At 12 h post-vaccination, significantly higher levels of fluorescence were detected in IN-caP vaccinated mice, compared to IN-aP mice (FIG. 6D). This suggests more DTaP particles were retained in the nasal cavity. This method resulted in the quantification of total particles in nasal cavity.

Figure 6E:
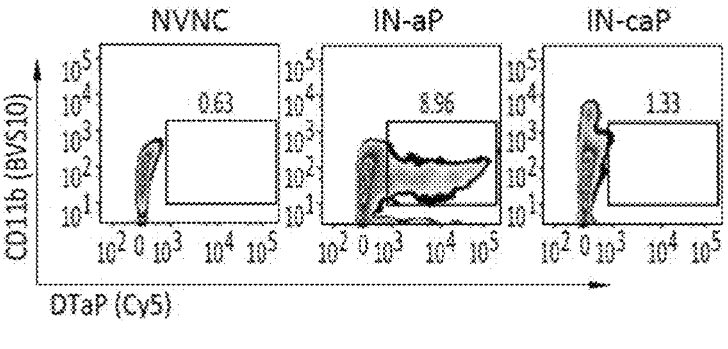
Figure 6F:
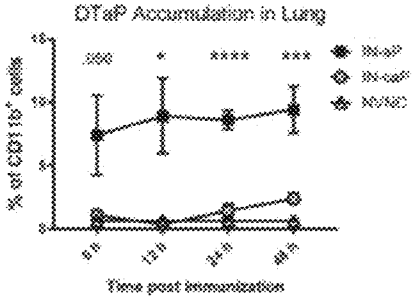

To quantify DTaP particles that were bound to innate immune cells flow cytometry was utilized. Single-cell suspensions were prepared from homogenized lung tissue and antigen presenting cells (APCs) bound to DTaP were quantified as live, single cells positive for $CD11b^+DTaP^+$(FIG. 6E). A significant increase in $CD11b^+$ cells that were bound to or contained DTaP particles was observed in IN-aP mice, compared to IN-caP (FIG. 6F). Together, these data suggest a higher deposition of DTaP in the lung with IN-aP when compared to IN-caP. Conversely, in the nasal cavity higher levels of DTaP was measured when mice were vaccinated with IN-caP, compared to IN-aP. These findings suggest that addition of curdlan to the DTaP vaccine causes retention in the nasal cavity, but without it, the vaccine components are more readily detected in the lung.

Figure 7A:
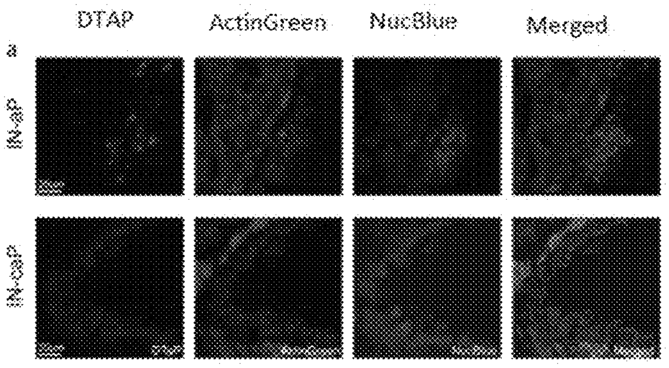
FIGS. 7A to 7D show acellular *pertussis* vaccine particle localization.
Figure 7B:
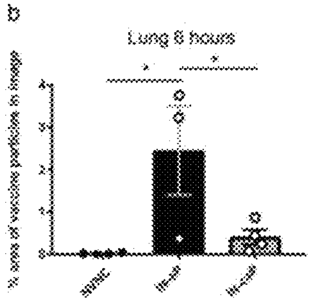
Figure 7C:
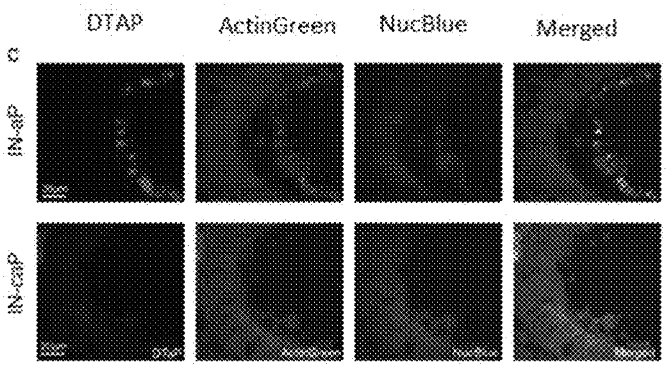
Figure 7D:
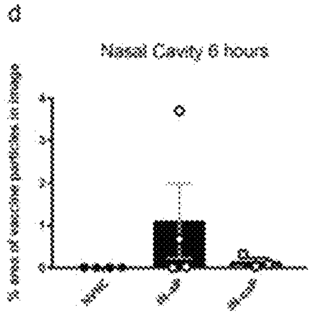

To visualize the deposition of DTaP particles, sections from the lung and nasal cavity were imaged using confocal microscopy. Vaccinated mice were euthanized after 6 h. Lung tissue was flash frozen, and skulls were embedded in paraffin for sectioning. Sections from the lung and nasal cavity were counterstained with NucBlue and ActinGreen to visualize epithelial tissue and fluorescent DTaP particles (FIG. 7A and FIG. 7C). Vaccine particles were quantified by measuring the percentage of total image field emitting DTaP fluorescence. A significant increase of fluorescent particles in the lungs of mice that were vaccinated with IN-aP was detected, compared to mice vaccinated with IN-caP (FIG. 7B). Using microscopy, there was no significant difference in the number of particles detected in the nostrils when comparing mice vaccinated with IN-aP to mice vaccinated with IN-caP (FIG. 7D). Interestingly, DTaP particles from the IN-aP vaccinated mice were localized in the lumen of the nasal passages, while particles from IN-caP vaccinated mice were deposited into the epithelial cells (FIG. 7C). Overall, these data suggest curdlan impacts localization of DTaP in the airway.

Example 4

Vaccination of Mice for with Genetically Detoxified *Pertussis* Toxoid

This example, and all subsequent examples, were carried out with genetically detoxified *pertussis* toxoid vaccines. PRN and PT antigens were obtained from List Biologicals and FHA antigen was obtained from ENZO bio.

The following vaccines were formulated:

aP vaccine: PRN, PT, and FHA antigens.

aP-alum: PRN, PT, and FHA antigens, with an aluminum hydroxide adjuvant.

aP-curdlan: PRN, PT, and FHA antigens, with a curdlan adjuvant, where the curdlan adjuvant is a medium molecular weight glucose polymer.

aP-β-glucan: PRN, PT, and FHA antigens, with a 1,3-β-glucan adjuvant, where the 1,3-β-glucan adjuvant is a whole glucan particle adjuvant having a particle size of 4 to 6 μm.

In aP-alum, the aluminum hydroxide adjuvant is an aluminum hydroxide wet gel suspension. The aluminum hydroxide induces a Th2 response by improving the attraction and uptake of antigen by antigen-presenting cells (APCs). Aluminum hydroxide particles have a net positive electrical charge at pH 5-7, and are attracted to negatively charged antigens.

CD-1 mice aged weeks were anesthetized with 77 mg/kg ketamine and 7.7 mg/kg xylazine. Mice were administered 50 μl of vaccine, with 25 μl into each nostril (IN). Four groups of mice (n=4) were vaccinated, with each group being vaccinated with one of the aP, aP-alum, aP-curdlan, and aP-β-glucan vaccines. Each vaccinated group of mice was given a boost vaccination 3 weeks later. At 10 weeks of age, the mice were challenged by exposure to *B. pertussis*. A fifth group of mice was mock-vaccinated with PBS, then challenged by exposure to *B. pertussis*. A sixth group of mice (NVNC) was mock-vaccinated with PBS, without being challenged by *B. pertussis*. Finally, a group of unvaccinated mice recovering from exposure to *pertussis* was examined (Convalescent mice).

Figure 8A:
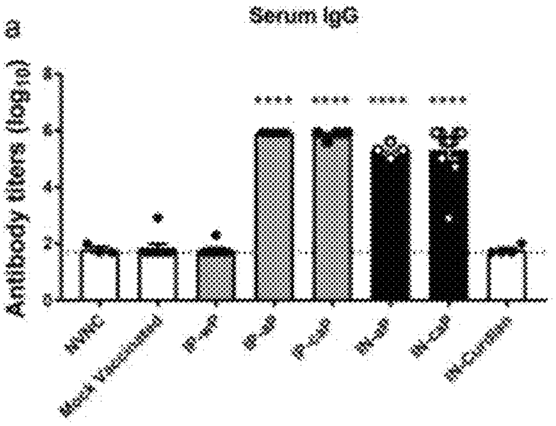
FIGS. 8A to 8D show production of anti-PT and anti-FHA IgG in serum induced by intranasal immunization. ELISAs were used to compare serological responses from mice immunized through IN or IP routes to mock vaccinated mice. Total IgG serum antibody titers from immunized and challenged mice were quantified at day 3 post challenge, where
Figure 8B:
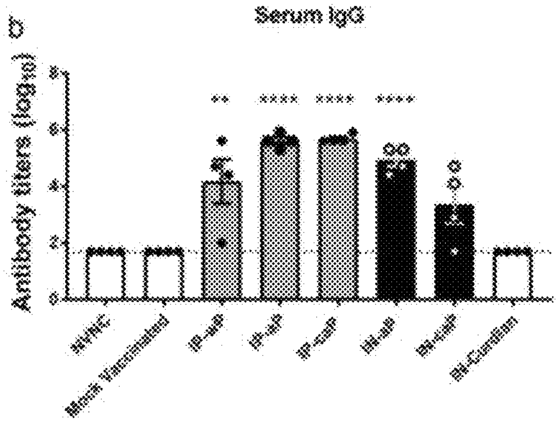
Figure 8C:
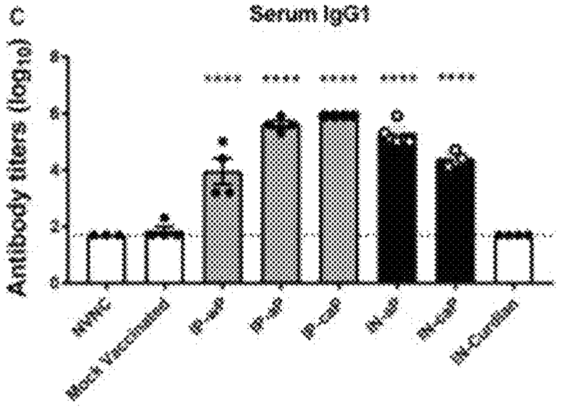
Figure 8D:
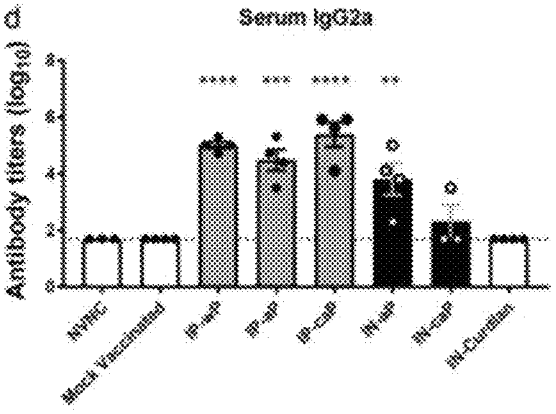

To determine if an IN-delivered *pertussis* vaccine would induce a systemic immune response, enzyme-linked immunosorbent assays (ELISAs) with serum from vaccinated and challenged mice against *B. pertussis* antigens found in the vaccine were performed. *Pertussis* toxin (PT) and filamentous hemagglutinin (FHA) antigens were tested. ELISAs were not performed against pertactin antigen, as 85% of current clinical isolates in the US do not express the protein. Serum anti-PT IgG titers were similar between mice immunized with IP-aP and those immunized through IN administration, as no significant differences were determined between IP-aP, IN-aP or IN-caP (FIG. 8A). A robust titer response to the bacterial adhesin FHA in IN vaccinated mice was observed. However, IN-aP serum anti-FHA titer was 7-fold higher than IN-caP (FIG. 8B). Induction of IgG1 antibodies (FIG. 8C) and IgG2a antibodies (FIG. 8D) by IN administration of DTaP (with or without curdlan) was studied to see if IN administration would lead to an increased Th1 immune response, resulting in a higher ratio of IgG2a compared to IgG1 antibodies. Neither the intranasal nor intraperitoneal route impacted the ratio of IgG2a to IgG1. Neither use of an aluminum hydroxide adjuvant (aP) nor a curdlan adjuvant (caP) impacted the ratio of IgG2a to IgG1.

Figure 9A:
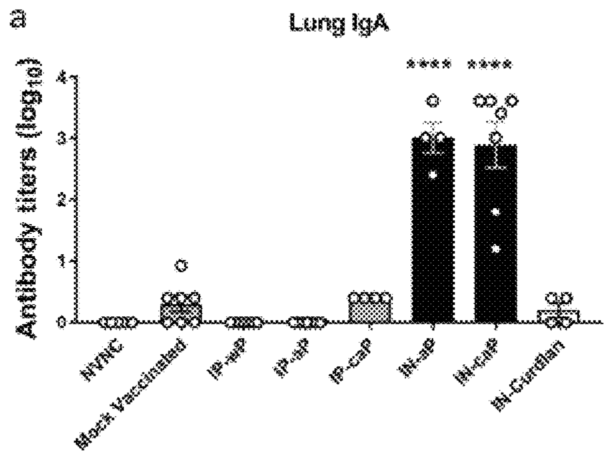
FIGS. 9A and 9B show that intranasal immunization induces production of anti-*B. pertussis* IgA in the respiratory system. ELISAs were performed using a lung homogenate supernatant (FIG. 9A) and a nasal lavage fluid (FIG. 9B) from vaccinated and challenged mice at day 3 post immunization. IgA titers were determined against whole-cell *B. pertussis* vaccine. Results are shown as averages of two independent experiments, represented on a log 10 scale for lung and linear scale of nasal lavage with mean±SEM (n=4-8). ****P<0.0001. P values were determined by one-way ANOVA with Dunnett's post hoc test compared to mock vaccinated mice.
Figure 9B:
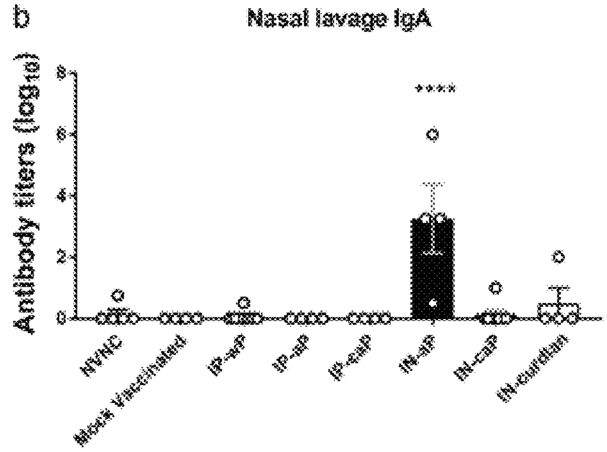

IgA antibodies and a local mucosal immune response in the lung and nasal cavity are important to *B. pertussis* immunization. The presence of IgA antibodies in the murine respiratory tissue due to IN immunization was measured. Using ELISAs, *B. pertussis*-specific IgA titers in homogenized lung tissue supernatant and nasal lavage fluid were measured. A robust IgA response was observed in the lung only when mice were immunized through the IN route (FIG. 9A). Similar results were not observed after intraperitoneal immunization. Antigen-specific IgA response was also not observed in mice immunized with curdlan alone. Detectable IgA *B. pertussis*-titer was observed in the nasal lavage fluid from both IN-aP and IN-caP vaccinated groups, although only IN-aP resulted in a significant increase compared to baseline levels (FIG. 9B). The presence of *B. pertussis* binding IgA in the lungs and nasal cavity suggests that IN DTaP is capable of priming a mucosal immune response in the upper and lower murine respiratory systems.

Figure 10A:
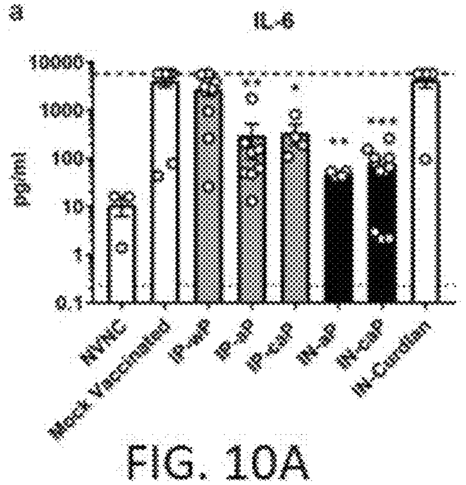
FIGS. 10A to 10D show that intranasal immunization decreases pulmonary pro-inflammatory cytokines during challenge. Analysis of cytokines from supernatant of lung homogenate at day 3 pc. Cytokines IL-6 (FIG. 10A), IFN-γ (FIG. 10B), IL-5 (FIG. 10C), and IL-17A (FIG. 10D) were quantified by electrochemiluminescence assay. Results shown as mean±SEM (n=4-8), *P<0.05, P<0.01, *P<0.001, ****P<0.0001. P values were determined by one-way ANOVA with Dunnett's post hoc test compared to mock vaccinated mice. Bars connecting groups indicate values determined by two-tailed un-paired t-test. Upper and lower limits of detection shown as dash or dotted lines, respectively, if data points reached these limits.
Figure 10B:
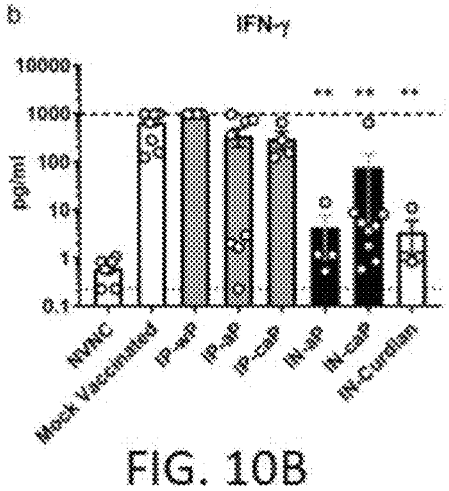
Figure 10C:
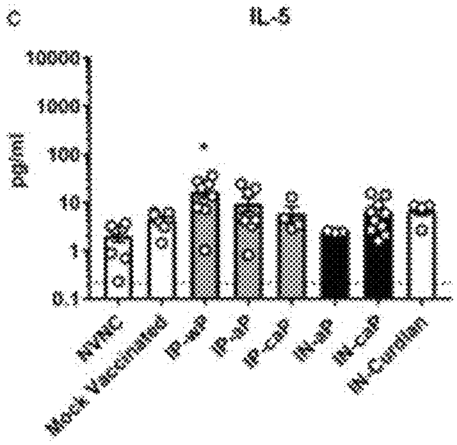
Figure 10D:
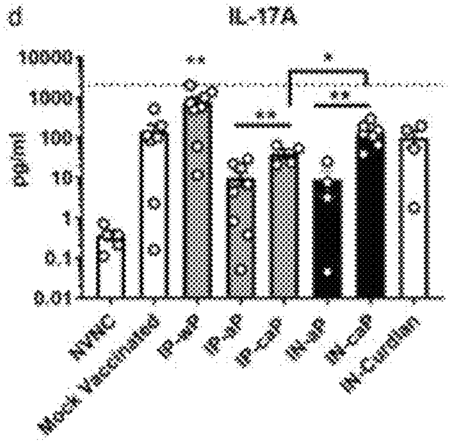

Neutralization of PT and inhibition of bacterial adhesins associated with DTaP protection leads to a reduced pro-inflammatory environment at the site of infection when compared to a natural infection. Conversely, challenge in whole-cell protected animals resulted in a severe pro-inflammatory response, similar to the natural infection of *B. pertussis*. To determine whether the immunostimulatory properties of curdlan would induce a more pro-inflammatory response following challenge with *B. pertussis* compared to IP-aP, cytokine concentrations were determined from supernatant of lung homogenate at day 3 post challenge. There is a significant reduction of IL-6 in the lungs of either IN-aP or IN-caP immunized mice when compared to mock vaccinated or IN-curdlan control mice, as shown in FIG. 10A. IL-6 levels are comparable to levels observed in IP immunized groups. A similar reduction in the Th1-associated cytokine IFN-γ and the cytokine IL-17A was observed in the IN administered groups, IN-aP and IN-caP; however, these levels were higher in IN-caP immunized mice (FIGS. 10B and 10D). A significant increase in the Th2-associated cytokine interleukin-5 and IL-17A was observed in IP-wP immunized mice, compared to mock vaccinated mice (FIGS. 10C and 10D). The whole cell vaccine (wP) also did not significantly reduce IL-6 or IFN-γ.

IN administration of curdlan, and moreover, vaccine administration through the IN route regardless of adjuvant has been shown to induce an increased IL-17 response. Levels of IL-17 in mice immunized with IN-caP were observed and compared to those in mice immunized with IN-aP or IP-aP. IL-17A in the lung supernatant was quantified, and significant increases of IL-17A with the addition of curdlan in IP-caP and IN-caP immunized mice were observed. When compared to IP-aP and IN-aP groups, IL-17A levels increased 4-fold and 14.9-fold, respectively (FIG. 10D). Furthermore, IN administration induced a significant increase in IL-17A compared to IP immunization. This IL-17A response was lower than the robust IL-17A induced by IP-wP (FIG. 10D).

Figure 11C:
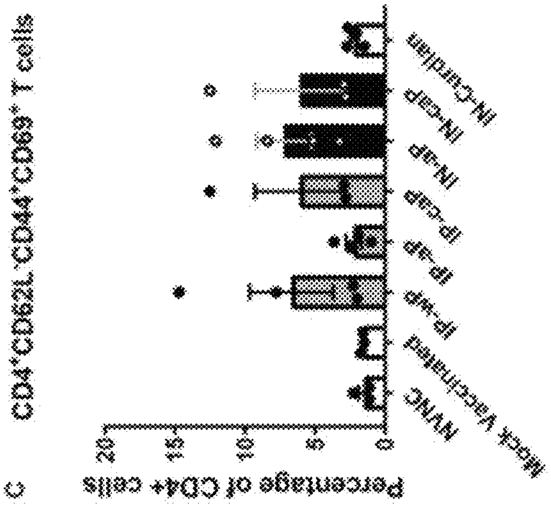
FIGS. 11A to 11C show that intranasal immunization reduced neutrophil accumulation in the lung and circulating neutrophils, but did not generate lung TRM population after *B. pertussis* challenge.
Figure 11B:
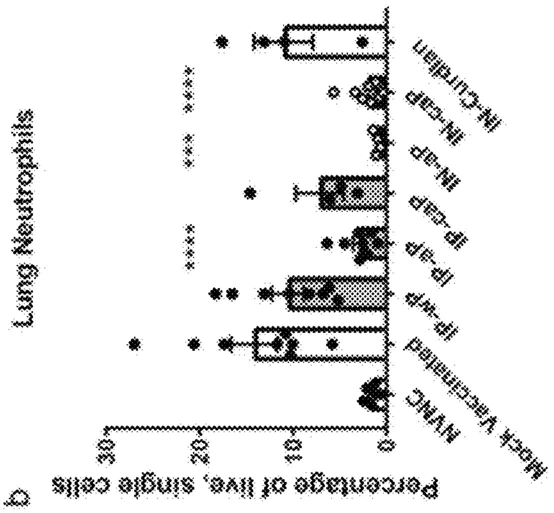
Figure 11A:
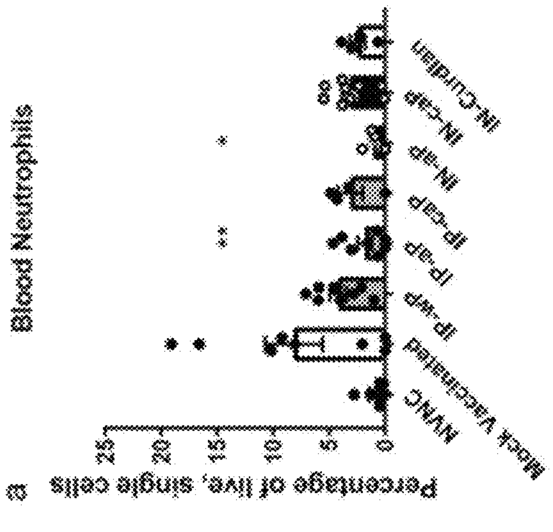
Figure 12A:
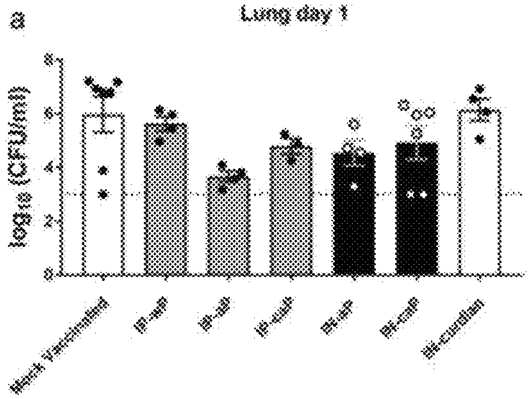
FIGS. 12A to 12F show that intranasal immunization reduced the respiratory *B. pertussis* bacterial burden. Analysis of bacterial burden was determined at days 1 and 3 pc. Bacteria were quantified by counting of serially diluted CFUs following immunization and challenge. CFU counts were determined from lung homogenate (FIGS. 12A and 12B), trachea homogenate (FIGS. 12C and 12D), and nasal lavage fluid (FIGS. 12E and 12F). Results are mean±SEM (n=4-8, with four averaged technical replicates) from two independent experiments. *P<0.05, P<0.01, *P<0.001, ****P<0.0001. P values were determined by one-way ANOVA with Tukey's post hoc test compared to mock vaccinated mice, or between connected columns. The dashed line represents the lower limits of detection due to plating.
Figure 12B:
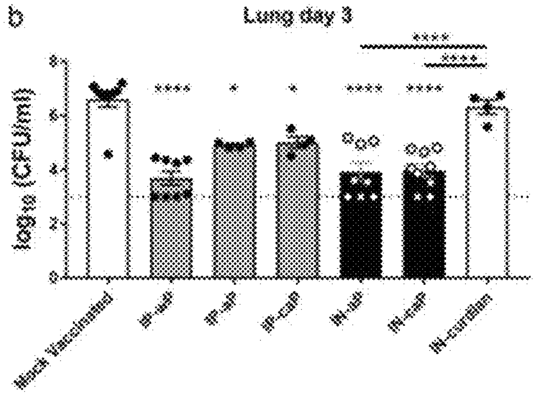
Figure 12C:
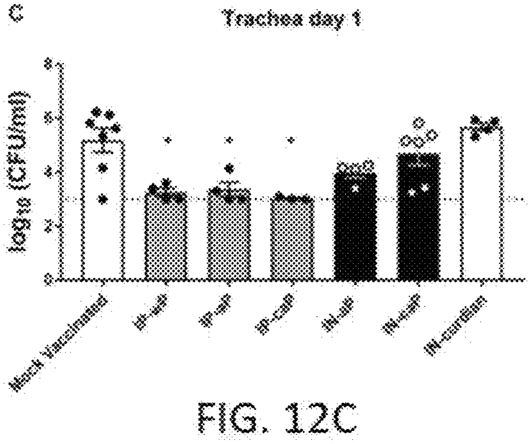
Figure 12D:
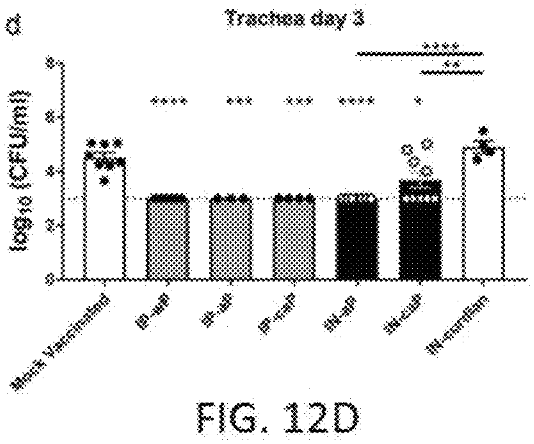
Figure 12E:
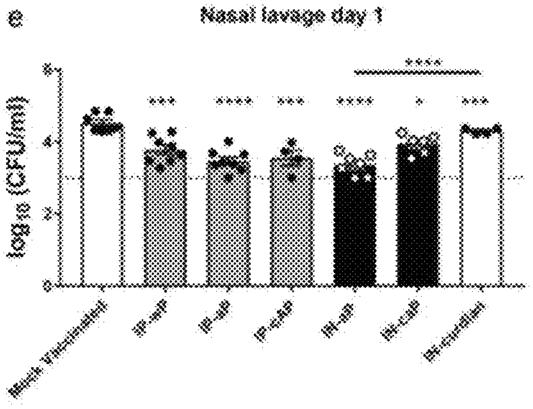
Figure 12F:
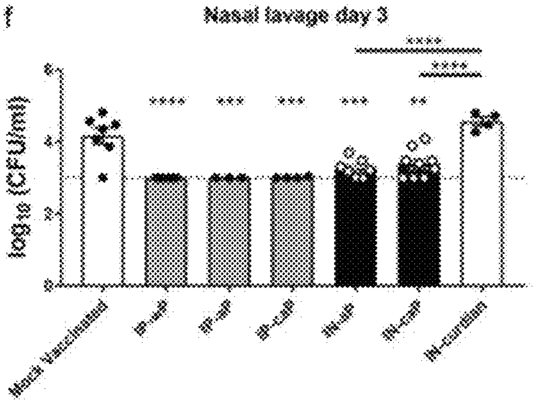

Natural infection with *B. pertussis* causes severe leukocytosis, which can be measured by elevated neutrophils in the peripheral blood. Following *B. pertussis* challenge, all vaccinated groups showed ameliorated symptoms of leukocytosis by day 3 pc; however, only the administration of DTaP either by IP or IN administration significantly reduced $CD11b^{+}Gr\text{-}1^{hi}$ neutrophils in the peripheral blood (FIG. 11A). In the lungs, neutrophils were decreased in IN-aP, IN-caP, and IP-aP immunized groups compared to mock vaccinated mice (FIG. 11B).

To determine if IN-aP or IN-caP could induce the expansion of a $T_{RM}$ population, population, CD4 T cells were isolated from the lung at day 3 pc, and were identified as $T_{RM}$ cells based on expression of surface markers: CD4+ CD62L−CD44+CD69+. We did not observe a statistical difference of this population following challenge with either IP or IN administered vaccines. However, we did observe a slight increase in IP-wP, IP-caP, IN-aP and IN-caP compared to mock vaccinated mice (FIG. 6*c*). Taken together these data suggest that immunization with DTaP through the IN route reduces the pro-inflammatory environment of the murine lung during *B. pertussis* challenge in a manner similar to IP-aP-mediated protection.

Lastly, the clearance of *B. pertussis* from the respiratory tract following IN immunization was examined. At days 1 and 3 pc, viable bacterial burden was quantified by counting of CFU in the lung, trachea, and nasal lavage fluid. A significant reduction in viable bacteria recovered from the lung was observed in all immunized groups by day 3 pc; however, these changes were not observed at day 1 pc (FIGS. 7A and 7B). In IN-aP and IN-caP immunized mice, bacterial burdens were reduced by 99.4% and 99.7%, respectively, compared to mock vaccinated mice. This reduction in viable bacterial burden was superior to that of mice immunized by IP-aP, an immunization that is known to be effective (FIG. 7B). This reduction in bacterial burden was not observed following immunization with the negative control (IN-curdlan), suggesting an antigen-specific response. Similar trends were observed in the trachea homogenate (FIGS. 7C and 7D), and in nasal lavage fluid (FIGS. 7E and 7F), as all immunized groups regardless of IP or IN delivery were significantly reduced compared to mock vaccinated mice. In summary, we observed similar clearance of *B. pertussis* from the respiratory tract of mice immunized intranasally, compared to mice immunized with vaccines known to be protective by the IP route.

Example 5

*Pertussis* patients and mice immunized with FauA peptides have anti-FauA antibodies. Mice were vaccinated with a set of six FauA-derived peptides (n=4), specifically SEQ ID NOS. 1 to 6 of Table 1; the peptides were conjugated to CRM197, a non-toxic mutant of diphtheria toxin. A set of unvaccinated control mice (n=4) was also tested. FIG. 13A shows ELISA detection of IgG antibodies in mice vaccinated with FauA peptides (n=4), where the antibodies bind to peptides having one of SEQ ID NOS. 1 to 6. These antibodies are not found in unvaccinated control mice. FIG. 13A also shows that convalescent *pertussis* patients (n=23) have sera which contain FauA antibodies which recognize FauA-derived peptides having SEQ ID NOS. 1 to 6. Again, these antibodies are not found in sera from control patients (n=12).

FIG. 13B shows ELISA detection of IgG which bind the individual FauA peptides of SEQ ID NOS. 1 to 6 in convalescent or control patient sera. The control patients did not have antibodies which recognized the FauA peptides. Antibodies which recognized each FauA peptide of Table 1 (SEQ ID NOS. 1 to 6) were detected in the convalescent patients.

Example 6

Vaccination of Mice for Vaccine Particle Tracking

CD-1 (outbred; strain code 022) mice aged four weeks were anesthetized with 77 mg/kg ketamine and 7.7 mg/kg xylazine. Mice were administered 50 μl of PBS control or an aP vaccine with PT, FHA, and PRN antigens, with 25 μl into each nostril (IN). After 21 days, a similar boost vaccine was administered into each nostril. Mice were divided into the following groups (n=4 for each group):

NVNC: PBS Control;
Mock-Vac: PBS Control;
aP: aP vaccine;
aP-alum: aP vaccine with an aluminum hydroxide adjuvant;
aP-curdlan: aP vaccine with a curdlan adjuvant;
aP-β-glucan: aP vaccine with a 1,3-beta-glucan adjuvant; and
Convalescent: Unvaccinated mice recovering after a *B. pertussis* infection.

With the exception of the convalescent mice and NVNC mice, each group of mice was challenged by infection with *B. pertussis* 35 days after administration of the initial intranasal vaccination.

Three days post challenge, the respiratory track bacterial burden was measured for each group of mice except the unchallenged NVNC mice. Burden was measured by nasal lavage, and in the lungs and trachea, using techniques described above. Results are shown in FIGS. 14A to 14C. Use of a curdlan or 1,3-beta-glucan adjuvant produced similar results to use of an alum adjuvant.

Three days post challenge, total IgG serum titers to *B. pertussis* and IgG serum titers to the PT and FHA vaccine antigens were measured, and found to be significantly elevated after challenge in mice vaccinated intranasally with aP, aP-alum, aP-curdlan, and aP-β-glucan vaccines. Results are shown in FIGS. 15A, 15B, and 15C. Mice in the NVNC and Mock-Vac groups showed no antibodies to *B. pertussis* (FIG. 15A) or to the PT or FHA vaccine antigens (FIGS. 15B and 15C). Convalescent mice showed antibodies to *B. pertussis*, but to a lesser extent than any of the vaccinated groups (FIG. 15A). Convalescent mice showed no antibodies to the PT vaccine antigen (FIG. 15B), although they did show FHA antibodies.

Three days post challenge, production of the cytokine IL-6 in mice vaccinated intranasally with aP, aP-alum, aP-curdlan, and aP-β-glucan vaccines was comparable to IL-6 production in the unchallenged NVNC mice, as shown in FIG. 15C. Production of the cytokine IL-6 in Mock-Vac and convalescent mice was substantially higher than in any of the vaccinated groups of mice.

Example 7: Long-Term *Pertussis* Protection

A protocol for testing long-term protection against *pertussis* by intranasal vaccination is shown in FIG. 16. CD-1 (outbred; strain code 022) mice aged four weeks were anesthetized with 77 mg/kg ketamine and 7.7 mg/kg xylazine. Mice were administered 50 μl of PBS control or an aP vaccine with PT, FHA, and PRN antigens, with 25 μl into each nostril (IN). After 21 days, a similar boost vaccine was administered into each nostril. Levels of *B. pertussis* antibodies were measured 30 days after the initial prime vaccination, and at 30-day intervals thereafter (FIG. 17). Mice were divided into the following groups (n=4 for each group):

NVNC: PBS Control;
Mock-Vac: PBS Control;
aP: aP vaccine;
aP-alum: aP vaccine with an aluminum hydroxide adjuvant;
aP-curdlan: aP vaccine with a curdlan adjuvant;
aP-β-glucan: aP vaccine with a 1,3-beta-glucan adjuvant; and
Convalescent: Unvaccinated mice recovering after a *B. pertussis* infection.

As shown in FIG. 17, the prime-boost vaccination protocol significantly increased levels of antibodies against *B.*

*pertussis* in intranasally vaccinated mice for at least five months post-vaccination, when compared to NVNC mice or Mock-Vac mice (NVNC and Mock-Vac lines overlap). The prime-boost vaccination protocol significantly increased levels of antibodies against *B. pertussis* in intranasally vaccinated mice to levels comparable to those in convalescent mice.

Six months after the initial prime vaccination, mice in each group except convalescent mice and NVNC mice were challenged by *B. pertussis* infection. Three days post challenge, mice were euthanized, and the effect of the vaccine was tested, e.g., by flow cytometry or serology. As shown in FIG. 18, six months after vaccination, intranasal vaccination produced significant *B. pertussis* and PT antigen specific IgG titers in serum. These antibodies were not seen in NVNC mice or Mock-Vac mice. Convalescent mice did not show PT antigen specific antibodies, but did show *B. pertussis* antibodies.

As seen in FIG. 18, exposure to an aP vaccine alone, or to an aP vaccine in combination with aluminum hydroxide or curdlan, increases antibodies to the PT antigen significantly ($P<0.05$, compared to mock-vaccinated mice). Exposure to an aP vaccine in combination with 1,3-beta-glucan has a greater impact on levels of antibodies to the PT antigen ($P<0.01$, compared to mock-vaccinated mice). Further, the increase in total *B. pertussis* antibody titers in convalescent mice is significant, when compared to mock-vaccinated mice ($P<0.01$). As seen in FIG. 18, the increase in total *B. pertussis* antibody titers in mice treated with aP, aP-alum, or aP-curdlan vaccines is significant; however, it is less significant that the increase in *B. pertussis* antibody titers in convalescent mice ($P<0.05$ for the aP vaccine; $P<0.01$ for the convalescent mice). The increase in total *B. pertussis* antibody titers in mice vaccinated with an aP vaccine in combination with 1,3-beta-glucan is highly significant, when compared to mock-vaccinated mice ($P<0.001$). Based on these results, it appears that administration of an aP vaccine in combination with 1,3-beta-glucan increases antibody production more than administration of an aP vaccine alone or with aluminum hydroxide or curdlan.

Example 8: Antibody-Expressing Cells in the Bone Marrow of Vaccinated Mice

Antibody secreting cells (ASCs) are differentiated cells of the humoral immune response. ASCs differentiate from activated B cells in lymph nodes. Most of the circulating ASCs undergo apoptosis, but some ASCs migrate to the bone marrow (BM) and eventually mature into long-lived plasma cells (LLPCs). Accordingly, the bone marrow of mice vaccinated as in Example 6 was examined following euthanasia for the presence of ASCs which secrete *B. pertussis* antibodies.

An enzyme-linked immune absorbent spot (ELISpot) analysis was used for detecting antibody-secreting cells in bone marrow tissue, in response to *B. pertussis* infection. Data were recorded 3 days (FIG. 19A) and 7 days (FIG. 19B) post-challenge, as number of IgG spots per $3\times10^5$ cells. Intranasal vaccination with aP, aP-alum, and aP-β-glucan (shown as aP+IRI-1501) significantly increased the number of *B. pertussis* antibody-secreting cells in bone marrow. Moreover, intranasal vaccination with aP-alum and aP-β-glucan significantly increased the number of *B. pertussis* antibody-secreting cells in bone marrow by three days post-challenge, when compared to vaccination with the aP vaccine alone (FIG. 19A). By seven days post-challenge, Although the various embodiments have been described in detail with particular reference to certain aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A vaccine composition, comprising:

a *Bordetella pertussis* antigen, wherein the *Bordetella pertussis* antigen comprises an extracellular *pertussis* toxoid (PT), the adhesion protein filamentous hemagglutinin (FHA), or a combination thereof; and an effective adjuvant amount of a 1,3-beta-glucan/1,6-beta-glucan copolymer derived from baker's yeast with a particle size of 3 μm to 4 μm.

2. A vaccine composition, comprising:

a *Bordetella pertussis* antigen, wherein the *Bordetella pertussis* antigen comprises an extracellular *pertussis* toxoid (PT), the adhesion protein filamentous hemagglutinin (FHA), or a combination thereof; and an effective adjuvant amount of a beta-glucan polymer derived from baker's yeast with a particle size of 3 μm to 4 μm, wherein the beta-glucan polymer is a 1,3-beta-glucan polymer, a 1,3-beta-glucan/1,4-beta-glucan copolymer, a 1,3-beta-glucan/1,6-beta-glucan copolymer, or a mixture thereof.

3. The vaccine composition of claim 1, wherein the *Bordetella pertussis* antigen further comprises a compound selected from the group consisting of an extracellular toxoid, an adhesion protein, an outer membrane protein, a receptor protein, and mixtures thereof.

4. The vaccine composition of claim 1, wherein the *Bordetella pertussis* antigen further comprises at least one antigen selected from the group consisting of the adhesion protein fimbriae (FIM), the outer membrane protein pertactin (PRN), the siderophore receptor protein FauA, the xenosiderophore receptor protein BfeA, the hemophore receptor protein BhuR, and mixtures thereof.

5. The vaccine composition of claim 1, wherein the composition further includes an adenylate cyclase toxin (ACT) antigen.

6. The vaccine composition of claim 5, wherein the ACT antigen is a C-terminal repeats-in-toxin domain (RTX) of ACT.

7. The vaccine composition of claim 1, wherein the composition is formulated to induce a Th1/Th17 immune response.

8. The vaccine composition of claim 1, wherein the composition is formulated for intranasal administration.

9. The vaccine composition of claim 1, wherein the composition is formulated for parenteral administration by subcutaneous (SC) injection, transdermal administration, intramuscular (IM) injection, or intradermal (ID) injection.

10. The vaccine composition of claim 1, wherein the composition is formulated for non-parenteral administration by oral administration, intravaginal administration, pulmonary administration, ophthalmic administration, or rectal administration.

11. A method of immunizing a host against *pertussis* by administering the composition of claim 1 intranasally to the host.

12. The vaccine composition of claim 2, wherein the *Bordetella pertussis* antigen further comprises a compound selected from the group consisting of the adhesion protein fimbriae (FIM), the outer membrane protein pertactin (PRN), the siderophore receptor protein FauA, the xenosiderophore receptor protein BfeA, the hemophore receptor protein BhuR, and mixtures thereof.

13. The vaccine composition of claim 2, wherein the composition further includes an adenylate cyclase toxin (ACT) antigen.

14. The vaccine composition of claim 13, wherein the ACT antigen is a C-terminal repeats-in-toxin domain (RTX) of ACT.

15. The vaccine composition of claim 2, wherein the composition is formulated for intranasal administration.

16. The vaccine composition of claim 2, wherein the composition is formulated for parenteral administration by subcutaneous (SC) injection, transdermal administration, intramuscular (IM) injection, or intradermal (ID) injection.

17. The vaccine composition of claim 2, wherein the composition is formulated for non-parenteral administration by oral administration, intravaginal administration, pulmonary administration, ophthalmic administration, or rectal administration.

18. A vaccine composition, comprising a *Bordetella pertussis* antigen, and an effective adjuvant amount of a beta-glucan polymer, wherein the *Bordetella pertussis* antigen is selected from the group consisting of:

a fragment of siderophore receptor protein FauA selected from the group consisting of SEQ ID NO: 1, SEQ ID NO: 2, SEQ ID NO: 3, SEQ ID NO: 4, SEQ ID NO: 5, SEQ ID NO: 6, and combinations thereof;

a fragment of xenosiderophore receptor protein BfeA selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and combinations thereof;

a fragment of hemophore receptor protein BhuR selected from the group consisting of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, and combinations thereof; and mixtures thereof.

19. A vaccine composition, comprising a *Bordetella pertussis* antigen, wherein the *Bordetella pertussis* antigen is selected from the group consisting of:

a fragment of siderophore receptor protein FauA selected from the group consisting of SEQ ID NO: 1, SEQ ID NO: 2, SEQ ID NO: 3, SEQ ID NO: 4, SEQ ID NO: 5, SEQ ID NO: 6, and combinations thereof;

a fragment of xenosiderophore receptor protein BfeA selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and combinations thereof;

a fragment of hemophore receptor protein BhuR selected from the group consisting of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, and combinations thereof; and mixtures thereof.

20. The vaccine composition of claim 19, wherein the *Bordetella pertussis* antigen is selected from the group consisting of:

a fragment of siderophore receptor protein FauA selected from the group consisting of SEQ ID NO: 1, SEQ ID NO: 2, SEQ ID NO: 3, SEQ ID NO: 4, SEQ ID NO: 5, SEQ ID NO: 6, and combinations thereof.

21. The vaccine composition of claim 2, wherein the beta-glucan polymer is a 1,3-beta-glucan polymer.

* * * * *